United States Patent [19]
Carroll et al.

[11] Patent Number: 5,981,285
[45] Date of Patent: Nov. 9, 1999

[54] METHOD AND APPARATUS FOR DETERMINING ANTICOAGULANT THERAPY FACTORS

[76] Inventors: Wallace E. Carroll; R. David Jackson, both of 1556 San Leandro La., Santa Barbara, Calif. 93108

[21] Appl. No.: 09/127,423

[22] Filed: Jul. 31, 1998

Related U.S. Application Data

[63] Continuation-in-part of application No. 08/969,316, Nov. 13, 1997, abandoned, which is a continuation of application No. 08/734,343, Oct. 21, 1996, abandoned.

[51] Int. Cl.$^6$ .................................................. G01N 33/86
[52] U.S. Cl. .................. 436/69; 422/73; 435/2; 435/13; 435/288.7; 364/496; 364/497; 364/498; 364/499; 73/64.41; 73/413.07; 73/413.08; 73/413.09
[58] Field of Search ................................ 422/73; 436/69; 435/2, 13, 288.7; 364/496, 497, 498, 499; 73/64.41, 413.07, 413.08, 413.09

[56] References Cited

U.S. PATENT DOCUMENTS

| 3,458,287 | 7/1969 | Gross et al. | 436/69 |
|---|---|---|---|
| 3,593,568 | 7/1971 | Schmitz | 73/64.1 |
| 3,905,769 | 9/1975 | Carroll et al. | 356/39 |
| 4,217,107 | 8/1980 | Saito et al. | 436/69 |
| 4,279,616 | 7/1981 | Saito et al. | 23/230 B |
| 4,720,787 | 1/1988 | Lipscomb | 364/416 |
| 4,788,139 | 11/1988 | Ryan | 435/13 |
| 5,156,974 | 10/1992 | Grossman et al. | 436/69 |
| 5,188,940 | 2/1993 | Krause et al. | 436/69 |
| 5,197,017 | 3/1993 | Carroll et al. | 364/497 |
| 5,502,651 | 3/1996 | Carroll et al. | 364/509 |
| 5,526,111 | 6/1996 | Collins et al. | 356/39 |

OTHER PUBLICATIONS

Hirsh et al., "Special Report: A Simple System for the Derivation of International Normalized Ratios for the Reporting of Prothrombin Time Results with North American Thromboplastin Reagents;" Am. J. Clin. Pathol, 92, pp. 124–126, 1989.

Ebert Ray "PTs, PRs, ISIs, and INRs: A Primer on Prothrombin Time Reporting: Part I: Calibration of Thromboplastin Reagents and Principles of Prothrombin Time Reporting", Clinical Hemostasis Review vol. 7, No. 11, Nov. 1993.

Ebert, Ray PTs, PRs, ISIs, and INRs: A Primer on Prothrombin Time Reporting: Part II: Limitations of INR Reporting: Clinical Hemostasis Review, vol. 7, No. 12, Dec. 1993.

(List continued on next page.)

Primary Examiner—Jill Warden
Assistant Examiner—S. Carrillo
Attorney, Agent, or Firm—John F. A. Earley; John F. A. Earley III; Harding, Earley, Follmer & Frailey

[57] ABSTRACT

A method and apparatuses are disclosed for determining an anticoagulant therapy factor (ATF), a corrected anticoagulant therapy factor (CATF), and a modified anticoagulant therapy factor (MATF), all selectively used for monitoring oral anticoagulant therapy to help prevent excessive bleeding or deleterious blood clots that might otherwise occur before, during or after surgery. The anticoagulant therapy factor (ATF), the corrected anticoagulant therapy factor (CATF), and a modified anticoagulant therapy factor (MATF) are based upon disclosed methods for determining the fibrinogen transformation rate (FTR) which, in turn, is dependent on a maximum acceleration point for fibrinogen (FBG) conversion. The ATF, CATF, and MATF quantities are also based upon the prothrombin time (PT), but have no need for the difficulty to obtain prior art International Normalized Ratio (INR) and International Sensitivity Index (ISI) parameters. The International Normalized Ratio (INR) was created to relate all species' clotting material to human clotting material. The AFT, CATF, and MATF quantities embody only human clotting material. The ATF, CATF, and MATF quantities and International Normalized Ratio (INR) are, hereby, species specific and provide the same results.

24 Claims, 10 Drawing Sheets

OTHER PUBLICATIONS

Solymoss et al. Markers of In Vivo Activation of Coagulation Interrelationships change with Intensity of Oral Anticoagulation A.J.C.P, vol. 105 No. 3, pp. 293–297, Mar. 1996.

Medical Group Pathology Laboratory Protime INR Values, Jul. 1, 1990.

Fibrinogen Determinations: An Automated Photoelectric System, A.B. Glassman, J.H. Maylock, J.H. Hudson (1972).

Rapid Determination of Fibrinogen by Thrombokinetics, A.J.C.P. —vol. 61, Ethan A. Natelson and Denise F. Dooley (Jun. 1974) pp. 828–833.

Research Communications in Molecular Pathology & Pharmacology, Rapid Fibrinogen Determination with the Prothrombin Time Using a Potentiophotometer, vol. 86, No. 1, Jul. 1995.

"Baxter Diagnostics, Inc. —Dade Determination of INR (International Normalized Ratio", Aug. 1994.

Baxter Diagnostics, Inc.—Dade Determination of INR (International Normalized Ratio), Jan. 1992.

5,981,285

METHOD AND APPARATUS FOR DETERMINING ANTICOAGULANT THERAPY FACTORS

CROSS-REFERENCE TO RELATED APPLICATIONS

This is a continuation-in-part application of U.S. patent application Ser. No. 08/969,316 filed Nov. 13, 1997 which is now abandoned, and which, in turn, is a continuation of U.S. patent application Ser. No. 08/734,343 filed Oct. 21, 1996 which is now abandoned.

BACKGROUND OF THE INVENTION

1. Field of the Invention

This invention relates to a relatively simple, yet accurate method and apparatus for monitoring oral anticoagulant therapy that takes into account varying prothrombin times caused by different sensitivities of various thromboplastin formed from rabbit brain, bovine brain, or other sources all used for oral anticoagulant therapy.

2. Description of the Prior Art

To prevent excessive bleeding or deleterious blood clots, a patient may receive oral anticoagulant therapy before, during and after surgery. To assure that the oral anticoagulant therapy is properly administered, strict monitoring is accomplished and is more fully described in various medical technical literature, such as the articles entitled "PTs, PR, ISIs and INRs: A Primer on Prothrombin Time Reporting Parts I and II" respectively published November, 1993 and December, 1993 issues of *Clinical Hemostasis Review*, and herein incorporated by reference.

These technical articles disclose anticoagulant therapy monitoring that takes into account three parameters which are: International Normalized Ratio (INR), International Sensitivity Index (ISI) and prothrombin time (PT), reported in seconds. The prothrombin time (PT) indicates the level of prothrombin in a plasma sample and is a measure of the coagulation response of a patient. The INR and ISI parameters are needed so as to take into account various differences in instrumentation, methodologies and in thromboplastins' (Tps) sensitivities used in anticoagulant therapy. In general, thromboplastins (Tps) used in North America are derived from rabbit brain, those previously used in Great Britain from human brain, and those used in Europe from either rabbit brain or bovine brain. The INR and ISI parameters take into account all of these various different factors, such as the differences in thromboplastins (Tps), to provide a standardized system for monitoring oral anticoagulant therapy to reduce serious problems related to prior, during and after surgery, such as excessive bleeding or the formation of blood clots.

As reported in Part I (Calibration of Thromboplastin Reagents and Principles of Prothrombin Time Report) of the above technical article of the *Clinical Hemostasis Review*, the determination of the INR and ISI parameters are quite involved, and as reported in Part II (Limitation of INR Reporting) of the above technical article of the *Clinical Hemostasis Review*, the error yielded by the INR and ISI parameters is quite high, such as about 13%. The complexity of the interrelationship between the International Normalized Ratio (INR), the International Sensitivity Index (ISI) and the patient's prothrombin time (PT) may be given by the below expression (1), wherein the quantity $$\left[\frac{\text{Patient's } PT}{\text{Mean of } PT \text{ Normal Range}}\right]$$

is commonly referred to as prothrombin ratio (PR):

$$INR = \left[\frac{\text{Patient's } PT}{\text{Mean of } PT \text{ Normal Range}}\right]^{ISI} \quad (1)$$

The possible error involved with the use of International Normalized Ratio (INR) is also discussed in the technical article entitled "Reliability and Clinical Impact of the Normalization of the Prothrombin Times in Oral Anticoagulant Control" of E. A. Loeliger et al, published in *Thrombosis and Hemostasis* 1985; 53: 148–154, and herein incorporated by reference. As can be seen in expression (1), ISI is an exponent of INR which leads to the possible error involved in the use of INR to be about ±13.5% or possibly even more. A procedure related to the calibration of the ISI is described in a technical article entitled "Failure of the International Normalized Ratio to Generate Consistent Results within a Local Medical Community" of V. L. Ng et al, published in Am. J. Clin Pathol 1993; 99: 689–694, and herein incorporated by reference.

The unwanted INR deviations are further discussed in the technical article entitled "Minimum Lyophilized Plasma Requirement for ISI Calibration" of L. Poller et al published in *Am J Clin Pathol* February 1998, Vol. 109, No. 2, 196–204, and herein incorporated by reference. As discussed in this article, the INR deviations became prominent when the number of abnormal samples being tested therein was reduced to fewer than 20 which leads to keeping the population of the samples to at least 20. The paper of L. Poller et al also discusses the usage of 20 high lyophilized INR plasmas and 7 normal lyophilized plasmas to calibrate the INR. Further, in this article, a deviation of +/− 10% from means was discussed as being an acceptable limit of INR deviation. Further still, this article discusses the evaluation techniques of taking into account the prothrombin ratio (PR) and the mean normal prothrombin time (MNPT), i.e., the geometric mean of normal plasma samples.

The discrepancies related to the use of the INR are further studied and described in the technical article of V. L. NG et al entitled, "Highly Sensitive Thromboplastins Do Not Improve INR Precision," published in *American Journal of Clinical Pathology*, 1998; 109, No. 3, 338–346 and herein incorporated by reference. In this article, the clinical significance of INR discordance is examined with the results being tabulated in Table 4 therein and which are analyzed to conclude that the level of discordance for paired values of individual specimens tested with different thromboplastins disadvantageously range from 17% to 29%.

It is desired that a method for monitoring oral anticoagulant therapy be provided that does not have the drawbacks of requiring the determination of the INR and ISI parameters and that does not suffer from the relatively high (13%) error sometimes occurring because of the use of these INR and ISI parameters with the exponents used in their determination.

Accordingly, it is a primary object of the present invention to provide a method and apparatus therefor, for accurate, yet simple, monitoring of oral anticoagulant therapy without any of the drawbacks and disadvantages of the prior art monitoring that relied on the INR and ISI parameters.

This invention relates to the inventions disclosed in U.S. Pat. Nos. 3,905,769 ('769) of Sep. 16, 1975; 5,197,017

('017) dated Mar. 23, 1993; and 5,502,651 ('651) dated Mar. 26, 1996, all issued to Wallace E. Carroll and R. David Jackson, and all of which are incorporated herein by reference. Further, the invention relates to the previously mentioned cross-referenced applications. The present application discloses a method and an apparatus for monitoring anticoagulant therapy that uses some of the features of the apparatus shown and described in all of the earlier patents.

SUMMARY OF THE INVENTION

The present invention is directed to methods and apparatuses for monitoring anticoagulant therapy so as to serve to prevent excessive bleeding or deleterious blot clots of a patient before, during and after surgery. More particularly, the present invention provides methods and apparatuses that are independent of the contributions made by the thromboplastins (Tps) and, thus, are devoid of the need of taking into account the effects of various thromboplastins (Tps) derived from rabbit brain or bovine brain. Specifically, the present invention provides methods and apparatuses therefor that derive anticoagulant therapy factors that replace the International Normalized Ratio (INR) determination used for monitoring oral anticoagulant therapy.

The methods and apparatuses of the present invention are used to determine anticoagulant therapy factors which are designated herein and are dependent on the prothrombin time (PT), the prothrombin ratio (PR), a fibrinogen transformation rate (FTR), and a maximum acceleration point (MAP) having an associated time to maximum acceleration (TMA). The anticoagulant therapy factors rates comprise a predetermined range starting prior to and ending after a maximum acceleration point which corresponds to the maximum acceleration of the fibrinogen (FBG) to fibrin conversion.

DETAILED DESCRIPTION

Figure 1:
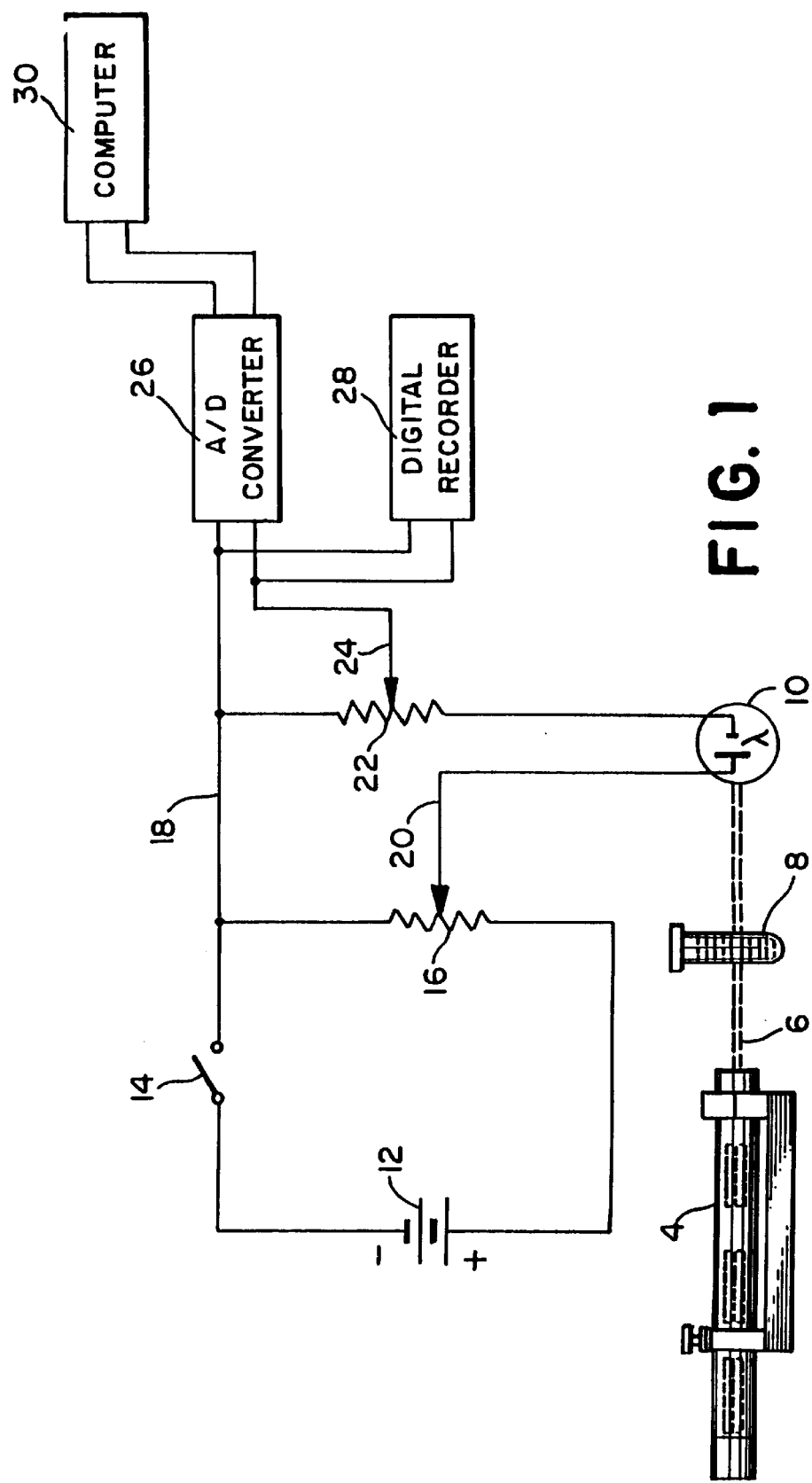
FIG. 1 is a diagram of potentiophotometric (hereinafter sometimes referred to as "POTENS +") anticoagulant therapy factor (ATF) determination apparatus generally similar to that shown in FIG. 1 of U.S. Pat. Nos. 3,905,769, 5,197,017 and 5,502,651, with the output of the analog/digital (A/D) converter being applied to a computer.

Referring to the drawings, wherein the same reference numbers indicate the same elements throughout, there is shown in FIG. 1 a light source 4 which may be a low power gas laser producing a beam of light 6 which passes through a sample test tube or cuvette 8 and is received by detection means which is preferably a silicon or selenium generating photocell 10 (photovoltaic cell). Battery 12 acts as a constant voltage DC source. Its negative terminal is connected through switch 14 to one end of variable resistor 16 and its positive terminal is connected directly to the opposite end of variable resistor 16. The combination of battery 12 and variable resistor 16 provides a variable DC voltage source, the variable voltage being derivable between line 18 at the upper terminal of resistor 16 and wiper 20. This variable DC voltage source is connected in series with detection means photocell 10, the positive output of detection means photocell 10 being connected to the wiper 20 of variable resistor 16 so that the voltage produced by the variable voltage DC source opposes the voltage produced by the detection means photocell 10. The negative output of detection means photocell 10 is connected through variable resistor 22 to line 18. Thus, the voltage across variable resistor 22 is the difference between the voltage produced by the variable voltage DC source and the voltage produced by the photovoltaic cell 10. The output of the electrical network is taken between line 18 and wiper 24 of variable resistor 22. Thus, variable resistor 22 acts as a multiplier, multiplying the voltage produced as a result of the aforesaid subtraction by a selective variable depending on the setting of variable resistor 22. The potentiophotometer just described embodies the electrical-analog solution to Beer's Law and its output is expressed directly in the concentration of the substance being measured.

In the present invention, wiper 24 is placed at a position to give a suitable output and is not varied during the running of the test. The output between line 18 and wiper 24 is delivered to an A/D converter 26 and digital recorder 28. As is known, the A/D converter 26 and the digital recorder 28 may be combined into one piece of equipment and may, for example, be a device sold commercially by National Instrument of Austin, Texas as their type Lab-PC+. The signal across variable resistor 22 is an analog signal and hence the portion of the signal between leads 18 and wiper 24, which is applied to the A/D converter 26 and digital recorder 28, is also analog. A computer 30 is connected to the output of the A/D converter 26, is preferably IBM compatible, and is programmed in a manner described hereinafter.

The description of the present invention makes reference to terms, and symbols thereof, having a general description as used herein, all to be further described and all of which are given in Table 1.

TABLE 1

| SYMBOL | TERM | GENERAL DESCRIPTION |
| --- | --- | --- |
| PT | Prothrombin Time | A period of time calculated from the addition of thromboplastin to a point where the conversion of Fibrinogen to Fibrin begins. |
| TMA | Time to Maximum Acceleration | The time from PT to a point where the rate of conversion of Fibrinogen to Fibrin has reached maximum and begins to slow. |
| FTR | Fibrinogen Transformation Ratio | The amount of Fibrinogen converted during a time period from -½ TMA to +½ TMA. This is a percentage of the total Fibrinogen. |

TABLE 1-continued

| SYMBOL | TERM | GENERAL DESCRIPTION |
|---|---|---|
| ATF | Anticoagulation Therapy Factor | The calculated value used to monitor the uses of an anticoagulant without a need for an International Sensitivity Index of a thromboplastin. |
| CATF | Corrected ATF | Change to the ATF calculation to give a better correlation of ATF vs. INR. |
| MATF | Modified ATF | A geometric modification making the value ATF equal to the value INR. |
| PR | Prothrombin Ratio | A value computed by dividing a sample PT by the geometric mean of at least 20 normal patients (MNPT). |

The present invention in one embodiment determines an anticoagulant therapy factor (ATF) and in another embodiment determines a corrected anticoagulant therapy factor (CATF) both selectably used as a standard during the monitoring of oral anticoagulant therapy without the need of any consideration of the International Normalized Ratio (INR) or International Sensitivity Index (ISI) previously discussed in already incorporated reference technical articles entitled PTs, PRs, ISIs and INRs: A Primer on Prothrombin Time Reporting Part I and II respectively published November, 1993 and December, 1993 issues of *Clinical Hemostasis Review*. The practice of the present invention relies upon the prothrombin time (PT) and a fibrinogen transformation rate (FTR), that is, the thrombin activity in which fibrinogen (FBG) is converted to fibrin to cause clotting in blood plasma. The practice of the present invention also relies upon a particular understanding of the enzymatic clotting steps occurring during a prothrombin time (PT) of plasma having proteins including factors II, IIa, V, VII, and X.

More particularly, during the clotting steps used to determine the clotting process of a plasma specimen of a patient under observation, a thromboplastin (Tp) activates factor VII which, activates factor X, which, in turn, under catalytic action of factor V, activates factor II (sometimes referred to as prothrombin) to cause factor IIa (sometimes referred to as thrombin) that converts fibrinogen (FBG) to fibrin with resultant turbidity activity which is measured, in a manner as to be described hereinafter, when the reaction is undergoing simulated zero-order kinetics.

From the above, it should be noted that the thromboplastin (Tp) does not take part in the reaction where factor IIa (thrombin) converts fibrinogen (FBG) to fibrin which is deterministic of the clotting of the plasma of the patient under consideration. The thromboplastin (Tp) only acts to activate factor VII to start the whole cascade rolling. Note also that differing thromboplastins (Tps) have differing rates of effect on factor VII, so the rates of enzyme factor reactions up to II–IIa (the PT) will vary. Therefore, the prothrombin times (PTs) vary with the different thromboplastins (Tps) which may have been a factor that mislead authorities to the need of taking into account the International Normalized Ratio (INR) and the International Sensitivity Index (ISI) to compensate for the use of different types of thromboplastins (Tps) during the monitoring of oral anticoagulant therapy. Note further, that thromboplastins (Tps) have nothing to do with factor IIa converting fibrinogen (FBG) to fibrin, so it does not matter which thromboplastin is used when the fibrinogen transformation is a primary factor. All that the thromboplastin (Tp) is needed for in the present invention is to start the reactions that give factor IIa. Once the present invention obtains the factor IIa, fibrinogen (FBG) to fibrin conversion goes on its own independent of the thromboplastin (Tp) used. Accordingly, the present invention in its anticoagulant therapy factor (ATF) embodiment needs only take into account the determination of the fibrinogen transformation rate (FTR), the prothrombin time (PT) and the maximum acceleration point (MAP), all of which may be typically ascertained by the use of fibrinogen solutions.

The practice of the present invention preferably includes fibrinogen (FBG) standard solutions and a control solution, wherein the fibrinogen standard solutions act as dormant references to which solutions analyzed by the present invention are compared, whereas the control solution acts as a reagent that is used to control a reaction related to the present invention. The fibrinogen standards include both high and low solutions, whereas the control solution is particularly used to control clotting times and fibrinogens of blood samples.

A fibrinogen (FBG) solution of 10 g/l may be prepared from a cryoprecipitate. The cryoprecipitate may be prepared by freezing plasma, letting the plasma thaw in a refrigerator and then, as known in the art, expressing off the plasma so as to leave behind the residue cryoprecipitate. The gathered cryoprecipitate should contain a substantial amount of both desired fibrinogen (FBG) and factor VIII (antihemophilic globulin), along with other elements that are not of particular concern to the present invention. The 10 g/l fibrinogen (FBG) solution, after further treatment, serves as the source for the high fibrinogen (FBG) standard. A 0.5 g/l fibrinogen (FBG) solution may then be prepared by a 1:20 (10 g/l/20= 0.5 g/l) dilution of some of the gathered cryoprecipitate to which may be added an Owren's Veronal Buffer (pH 7.35) (known in the art) or normal saline solution and which, after further treatment, may serve as a source of the low fibrinogen (FBG) standard. Then, 1 ml of each of the high (10 g/l) and low (0.5 g/l) sources of the fibrinogen standards may be added to 1 ml of normal human plasma (so the human plasma can clot), and this addition respectively may yield 6.38 g/l and 1.5 g/l high and low fibrinogen (FBG) standards, used in the practice of the present invention for analyzing samples of citrated blood under test, especially those samples being monitored during oral anticoagulant therapy which is of prime importance to the present invention.

As is known, the addition of the reagent Thromboplastin•C serves as a coagulant to cause clotting to occur within a sample of citrated blood under test which may be contained in a test tube 8. As clotting occurs, the A/D converter 26 of FIG. 1 will count and produce a digital value of voltage at a predetermined period, such as once every 0.05 or 0.01 seconds. As more fully described in the previously incorporated be reference U.S. Pat. No. 5,197,017 ('017), these voltage values are stored and then printed by the recorder as an array of numbers, the printing being from left to right and line by line, top to bottom. There are typically one hundred numbers in the five groups representing voltage values every second and hence, one line represents one-fifth of a second in time (20×0.01 seconds). Individual numbers in the same column are twenty sequential numbers apart. Hence, the time difference between two adjacent numbers in a column is one-fifth of a second. The significance of these recorded values may be more readily appreciated after a general review of the operating principles of the present invention illustrated in FIG. 2 having a Y axis identified as Fibrinogen Concentration (Optical Density) and a X axis identified in time (seconds).

Figure 2:
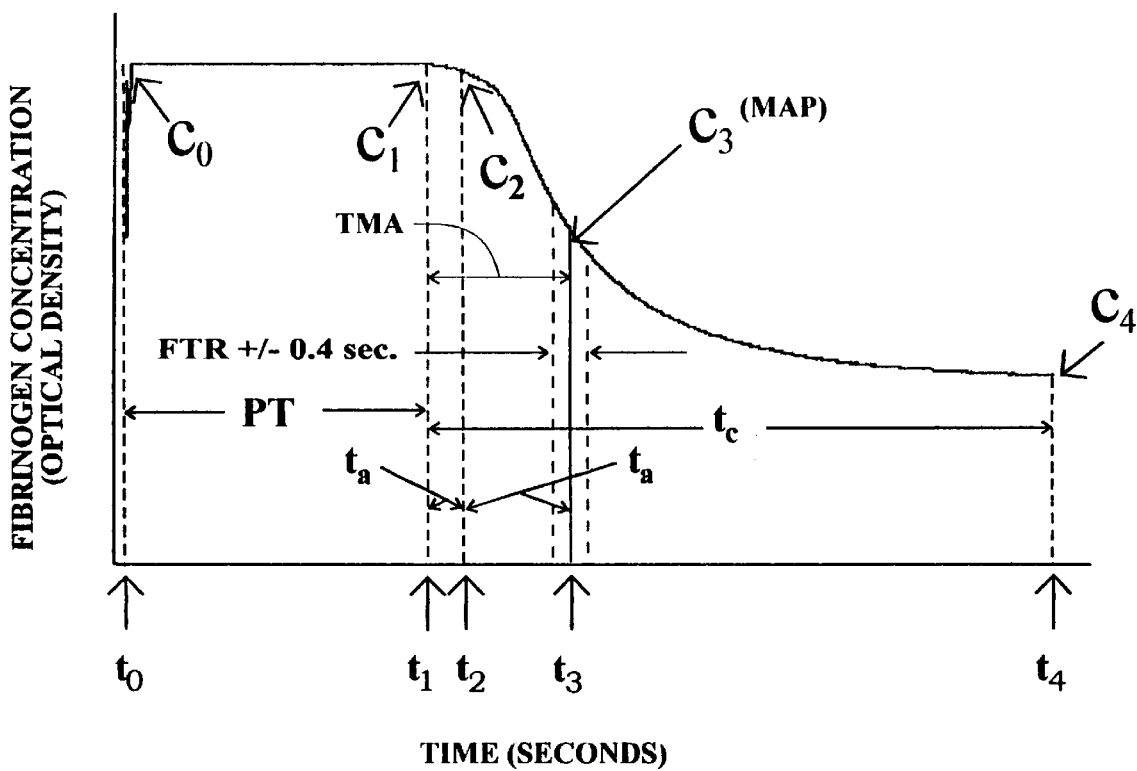
FIG. 2 is a plot of the various phases of the fibrinogen concentration occurring in a typical plasma clotting process.

FIG. 2 illustrates the data point locations of the clotting curve related to the present invention. In general, FIG. 2 illustrates a "clot slope" method that may be used in the present invention for determining an anticoagulant therapy factor (ATF) and is more fully discussed in the previously incorporated by reference U.S. Pat. No. 5,502,651 which measures the concentration of the fibrinogen (FBG) in the plasma that contributes to the clotting of the plasma and uses the potentiophotometer of FIG. 1 to provide an output voltage signal that is directly indicative of the fibrinogen (FBG) concentration in the plasma sample under test contained in a test tube 8. The quantities given along the Y-axis of FIG. 2 are values (+and−) that may be displayed by the digital recorder 28. The "clot slope" method comprises detection of the rate or the slope of the curve associated with the formation of fibrin from fibrinogen. The "clot slope" method takes into account the prothrombin time (PT) (previously mentioned as one of the factors for determining the anticoagulant therapy) which is typically defined as the time duration between the injection of a reagent, such as thromboplastin and calcium ion, into the plasma and the corresponding instant of time when the clotting process begins.

As seen in FIG. 2, at time $t_0$, corresponding to a concentration $c_0$, the thromboplastin/calcium ion reagent is introduced into the blood plasma which causes a disturbance to the composition of the plasma sample which, in turn, causes the optical density of the plasma to increase momentarily. After the injection of the reagent (the time of which is known, as to be described, by the computer 30), the digital quantity of the recorder 28 of FIG. 1 rapidly increases and then levels off in a relatively smooth manner and then continues along until the quantity $c_1$ is reached at a time $t_1$. The time which elapses between the injection of thromboplastin at $t_0$ and the instant time $t_1$ of the quantity $c_1$ is the prothrombin time (PT) and is indicated in FIG. 2 by the symbol PT. The prothrombin time (PT) is of primary importance because it is one of the three parameters (the other are the fibrinogen transformation rate (FTR) and the maximum acceleration point (MAP) having associated with it a time to maximum acceleration (TMA)) that determines the anticoagulant therapy factor (ATF) of the present invention.

The optical density of the quantity $c_1$ directly corresponds to a specified minimum amount of fibrinogen (FBG) that must be present for a measuring system, such as the circuit arrangement of FIG. 1, to detect that a clot is being formed. Further, all the quantities shown in FIG. 2 are of optical densities that are directly correlatable to fibrinogen concentration values. The critical quantity $c_1$, may vary from one clot detection system to another, but for the potentiophotometer system of FIG. 1, this minimum is defined by units of mass having a value of about 0.05 grams/liter (g/l).

The detection of this first predetermined quantity $c_1$ is shown in FIG. 2 to occur at an instant time $t_1$ which is the start of the clotting process being monitored by the method of the present invention for determining the anticoagulant therapy factor (ATF). The time $t_1$ is the beginning point of the fibrinogen formation, that is, it is the point that corresponds to the beginning of the acceleration of the fibrinogen conversion that lasts for a predetermined time, preferably about 1.5 seconds. This $t_1$ point is determined by a real time analysis of the optical density data accumulated during testing. The time duration of at least 1.5 seconds allows a sufficient amount of delay time to eliminate any false responses due to noises created by initial mixing of the reagent into the sample or bubbles within the sample under test. This 1.5 second duration helps determine the beginning point ($t_1$) of the fibrinogen conversion in spite of any bubbles or artifacts that might be present for short durations. These noise producers might, without the benefits of the present invention, be erroneously interpreted as early clots and might lead to a correspondingly false response by the instrument performing the measuring.

The acceleration of the fibrinogen conversion that occurs within the 1.5 second duration, is shown in FIG. 2 as a first time period $T_a$ ($t_1$ to $t_2$). This first time period $T_a$ is defined by the first quantity $c_1$ and a second $c_2$ occurring at a time $t_2$, wherein $c_2$ has a value equal to at least $c_1$. The acceleration of the fibrinogen conversion continues until a time $t_3$, having a corresponding quantity $c_3$. The time $t_3$, as well as the quantity $c_3$, is of primary importance to the present invention because it is the point of maximum acceleration of the fibrinogen (FBG) to fibrin conversion and is also the point where deceleration of fibrinogen (FBG) to fibrin conversion begins. Further, the elapsed time from $t_1$ to $t_3$ is a time to maximum acceleration (TMA), shown in FIG. 2, which serves as a multiplier (TMA)/100 to be described. The third quantity ($c_3$) and the time $t_3$ define a maximum acceleration point (MAP) associated with the present invention and is shown in FIG. 2 as having predetermined ranges starting prior to maximum acceleration point (MAP) and ending after the maximum acceleration point (MAP), with the difference covered by the overall range defining the fibrinogen transformation rate (FTR), which is also shown in FIG. 2 and has a typical band of +/−0.5 seconds. Fibrin formation, after a short lag phase before the MAP, occurs for a period of time, in a linear manner. Fibrinogen (FBG) is in excess during this lag phase, and fibrin formation appears linear up to the MAP. The FBG formed during an interval from +/−(TMA÷2) seconds of the MAP is given as a percentage of the total clottable FBG. This is the fibrinogen transformation rate (FTR). The fibrinogen transformation rate (FTR) is of primary importance to the present invention because it is one of the three parameters that determine the anticoagulant therapy factor (ATF) of the present invention with the other two being the prothrombin time (PT) and the maximum acceleration point (MAP). The predetermined range may be from about 0.1 seconds to about 5.0 seconds on each side of the maximum acceleration point (MAP) shown in FIG. 2 so that the fibrinogen transformation rate (FTR) may cover an overall difference from about 0.2 seconds to about 10.0 seconds.

The times $t_3$ and $t_2$ define a second time period $T_b$ which has a typical value of 1.5 seconds. The deceleration of fibrinogen (FBG) to fibrin conversion continues until a quantity $c_4$ is reached at a time $t_4$. The time $t_4$ is the point where the deceleration of the fibrinogen (FBG) to fibrin conversion corresponds to a value which is less than the required amount of fibrinogen (FBG) that was present in order to start the fibrinogen (FBG) to fibrin conversion process. Thus, because the desired fibrinogen (FBG) to fibrin conversion is no longer in existence, the time $t_4$ represents the ending point of the fibrinogen (FBG) to fibrin conversion as defined by the present invention. The fibrinogen (FBG) to fibrin conversion has a starting point of $t_1$ and an ending point of $t_4$. These times $t_1$ and $t_4$ define a third period $T_c$.

The significance of the points ($t_1$, and $t_4$) are not the times at which they occur, but rather the difference in the optical density of the quantities $c_1$ and $c_4$ occurring at the times $t_1$ and $t_4$. This difference is defined herein as the delta optical density of the "clot slope" method and is of importance to the present invention related to determining the anticoagulant therapy factor (ATF). The "clot slope" method that gathers typical data as shown in FIG. 2 has four critical parameters. The first is that the initial delta optical density of substance being analyzed should be greater than about 0.05 g/l in order for the circuit arrangement of FIG. 1 to operate effectively. Second, the acceleration (fibrinogen ((FBG)) to fibrin conversion associated with $T_a$) should be increasing for a minimum period of about 1.5 seconds so as to overcome any false reactions created by bubbles. Third, the total delta optical density (defined by the difference in quantities $c_1$ and $c_4$) should be at least three (3) times the instrument value in order to perform a valid test, i.e., (3)*(0.05 g/l)=0.15 g/l. Fourth, the fibrinogen (FBG) to fibrin conversion is defined, in part, by the point ($t_4$) where the deceleration of conversion becomes less than the instrument value of about 0.05 g/l that is used to detect the clot point ($t_1$). As with most clot detection systems, a specific amount of fibrinogen needs to be present in order to detect a clot forming. Adhering to the four given critical parameters allows the present invention to determine a specific quantity of fibrinogen. In order for that specific amount of fibrinogen to be determined, it is first necessary to detect a clot point ($t_1$). After that clot point ($t_1$) is detected, it logically follows that when the fibrinogen conversion becomes less than the specific amount (about 0.05 g/l for the circuit arrangement of FIG. 1), the end point ($t_4$) of the fibrinogen conversion has been reached.

The gathering, storing, and manipulation of the data generally illustrated in FIG. 2, is primarily accomplished by computer 30 of FIG. 1 that receives digital voltage values converted, by the A/D converter 26, from analog voltage quantities of the photocell 10 detection means.

The preferred IBM-compatible computer 30 of FIG. 1 stores and manipulates these digital values corresponding to related data of FIG. 2 and is preferably programmed as follows:

(a) with citrated blood, such as described above in the test tube 8, the computer 30, as well as the recorder 28, sequentially records voltage values for a few seconds before injection of thromboplastin. As previously discussed, thromboplastin is one of the factors in the human body that causes blood to clot. Prothrombin is another. Fibrinogen is yet another. Before injection of the thromboplastin, the output from the A/D converter 26 is relatively constant. When thromboplastin is injected into the blood in test tube 8, a significant and abrupt change occurs in the recorded voltage values of both the computer 30 and the recorder 28. This abrupt change is recognized by both the recorder 28 and, more importantly, by the computer 30 which uses such recognition to establish $t_0$ already discussed with reference to FIG. 2. The computer 30 may be programmed so as to correlate the digital quantities of the A/D converter 26 to the analog output of the detector means photocell 10 which, in turn, is directly correlatable to the fibrinogen (FBG) concentration g/l of the sample of blood discussed with reference to FIG. 2;

(b) following the recording of digital quantities representative of the fact that thromboplastin had been injected (see to of FIG. 2), the computer 30 may be programmed to look for a digital quantity representative of the previously discussed critical quantity $c_1$, and when such occurs, record its instant time $t_1$. The time span between $t_0$ and $t_1$ is the prothrombin time (PT) of particular importance to the present invention and has a normal duration of about 12 seconds, but may be greater than 30 seconds;

(c) following the detection of the critical quantity $c_1$, the computer 30 may be programmed to detect for the acceleration of fibrinogen (FBG) to fibrin conversion within the defined time period $T_a$, having a typical duration of 1.5 seconds. The parameters of this time period $T_a$ are its beginning which is defined by the occurrence ($t_1$) of the first predetermined quantity $c_1$ and its end which is defined by the second predetermined quantity $c_2$ occurring at time $t_2$. The first predetermined time period $T_a$ has a typical range of about 12 to about 30 seconds as measured from $t_0$. The computer 30 is also programmed to detect the maximum acceleration quantity $c_3$ and its time of occurrence $t_3$ (having a typical value of 1.5 seconds after $t_2$). These two times $t_2$ and $t_3$ define the time duration $T_b$. Furthermore, the computer detects the quantity $c_4$ occurring at time $t_4$ so as to define the time duration $T_c$. The time period $T_a$ may exceed but may not be less than the typical 1.5 second duration. The duration of the time between the occurrence ($t_1$) of the quantity $c_1$, and the occurrence ($t_2$) of the quantity $c_2$ is not fixed. It is only important that the rate of fibrin formation increase for at least 1.5 second following the occurrence of ($t_1$);

(d) following the detection of the maximum acceleration quantity $c_3$ and the time $t_3$ both of which define the maximum acceleration point (MAP), the computer 30 is programmed to determine the fibrinogen transformation rate (FTR) covering a predetermined range starting prior to the maximum acceleration point (MAP) and ending after the maximum acceleration point (MAP). The elapsed time from $t_1$ to $t_3$ is the time to maximum acceleration (TMA) shown in FIG. 2 and is a multiplier factor (TMA/100). The fibrinogen transformation rate (FTR) has an upwardly rising (increasing quantities) slope prior to the maximum acceleration point (MAP) and, conversely, has a downwardly falling (decreasing quantities) slope after the maximum acceleration point (MAP). The computer 30 is programmed to allow for a predetermined range defining the fibrinogen transformation rate (FTR) which may be from about 0.1 seconds up to 5.0 seconds on each side of the maximum acceleration point (MAP) so that the fibrinogen transformation rate (FTR) may cover an overall difference from about 0.2 seconds to about 10.0 seconds;

(e) following the detection of the acceleration of fibrinogen conversion, the computer 30 is programmed to detect for a deceleration of the fibrinogen conversion, wherein the fibrinogen concentration decreases from its third predetermined quantity $c_3$ to a fourth predetermined quantity $c_4$ having a value which is about equal but less than the first quantity $c_1$. The time duration from the instant time of the detection of the first quantity $c_1$ to the instant time of the detection of the fourth quantity $c_4$, defines the third period $T_c$;

(f) the computer 30 manipulates the collected data of (a); (b); (c); (d) and (e) above, to determine the prothrombin time (PT) based on the principle that if a required amount (e.g., 0.05 g/l) of fibrinogen concentration $c_1$ is first necessary to detect a clot point ($t_1$); then when the fibrinogen concentration ($c_4$) becomes less than the required amount $c_1$, which occurs at time ($t_4$), the fibrinogen end point has been reached. More particularly, the required fibrinogen concentration $c_1$ is the starting point of fibrinogen conversion of the clotting process and the less than required fibrinogen concentration $c_4$ is the end point of the fibrinogen conversion of the clotting process. Thus, the duration of the fibrinogen conversion of the clotting process of the present invention is defined by the time period between $t_1$ and $t_4$ and is generally indicated in FIG. 2 as $T_c$; and (g) the computer 30 now has the information needed to determine the anticoagulant therapy factor (ATF) of the present invention. More particularly, the computer 30 has knowledge of the fibrinogen transformation rate (FTR) and the prothrombin time (PT) and a simple division routine, run in the computer 30, the product which, when multiplied by the time to maximum acceleration (TMA), yields the anticoagulant therapy factor (ATF) of the present invention having the relationship given by the below expression (2):

$$ATF = PT/FTR*(TMA/100) \qquad (2)$$

It should now be appreciated that the practice of the present invention provides a relatively easy and automatic method for obtaining an anticoagulant therapy factor (ATF) without encountering the complications involved with obtaining the prior art quantities International Normalized Ratio (INR) and International Sensitivity Index (ISI) having a relationship defined by the below expression (3) as well as the quantity $$\left[\frac{\text{Patient's } PT}{\text{Mean of } PT \text{ Normal Range}}\right]$$

referred to as the prothrombin ratio (PR) all discussed in the "Background" section:

$$INR = \left[\frac{\text{Patient's } PT}{\text{Mean of } PT \text{ Normal Range}}\right]^{ISI} \qquad (3)$$

The anticoagulant therapy factor (ATF) is a replacement for the International Normalized Ratio (INR); however, the existing medical literature, instrumentation, and methodologies are closely linked to the International Normalized Ratio (INR) and, therefore, the practice of the present invention correlates, by comparative testing, the ATF to INR quantities to each other even with the understanding that the INR determination may have an error of about thirteen (13)% which needs to be taken into account to explain certain inconsistencies to be described hereinafter.

Comparative Testing of ATF and INR Quantities

Comparative testing was accomplished by using three different thromboplastins (Tps), the first being Dade Thromboplastin (Tp)•C with an ISI of 2.06; the second being Dade Innovin with an ISI of about 1.0; and the third being Sigma Diagnostics Thromboplastin with calcium ion and having an ISI of 2.48. The usage of these three thromboplastins (Tps) having calcium ion provided for a relatively large range of ISI parameters. Citrated patient's plasmas were obtained about one hour after the plasmas had been drawn from patients and having had their prothrombin time (PT) determined. Most of the patients were on the anticoagulant Coumadin and a very few were on both Coumadin and Heparin. After the prothrombin times were determined, the FTR and INR were determined in a manner as previously described. At least four runs (Tray I, Tray II, Tray III and Tray IV to be described, especially for FIGS. 3–8 also to be described) of comparative testing were accomplished. The Thromboplastin•C was used in the first run (Tray I) and its usage was repeated in the last run (Tray IV). The thromboplastin (Tp) Innovin was used for the second specimens (Tray II). The thromboplastin was changed to Sigma (Tp) (Tray III), and testing was again performed. Finally, Thromboplastin•C was used for Tray IV. It took about 40 minutes to change over the various thromboplastins and run the specimens (I, II, III and IV). Thromboplastin•C was run first (Tray I) and last (Tray IV) to show that significant coagulation factor deterioration had not occurred. The results of the comparative testing are shown on FIGS. 3–8, all of which have a X axis indicating values of the International Normalized Ratio (INR) and a Y axis indicating values of the anticoagulant therapy factor (ATF) and the correlation therebetween is the correlation factor, r, thereof.

Figure 3:
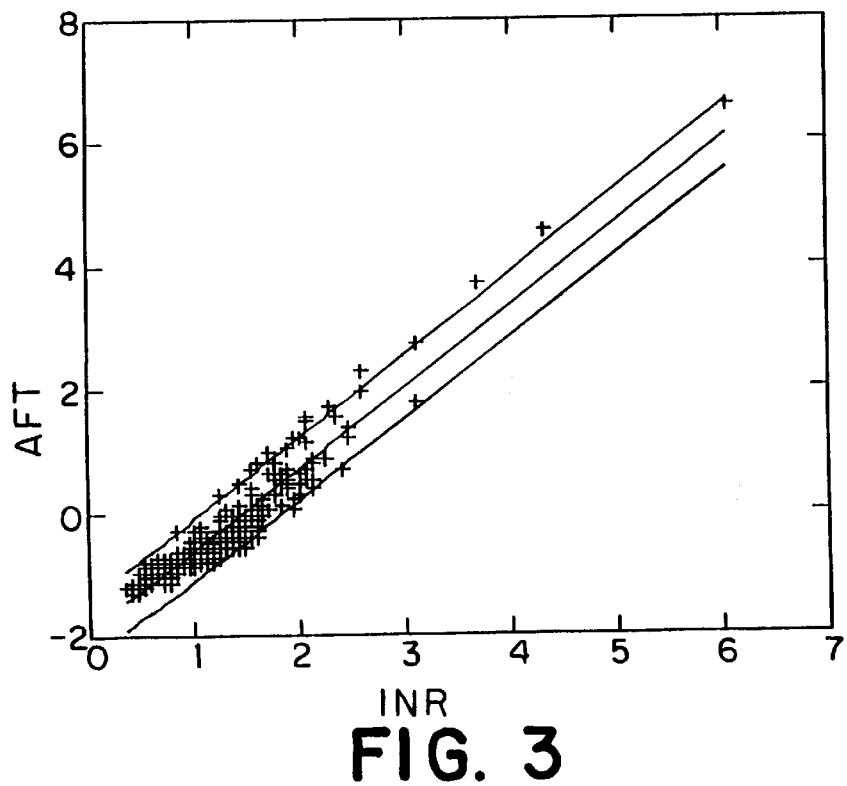
FIGS. 3 and 4 show the results of comparative testing between using a +/−0.5 second FTR range (FIG. 3) and a range of FTR of 1.0 seconds (FIG. 4) prior to the maximum acceleration point (MAP).
Figure 4:
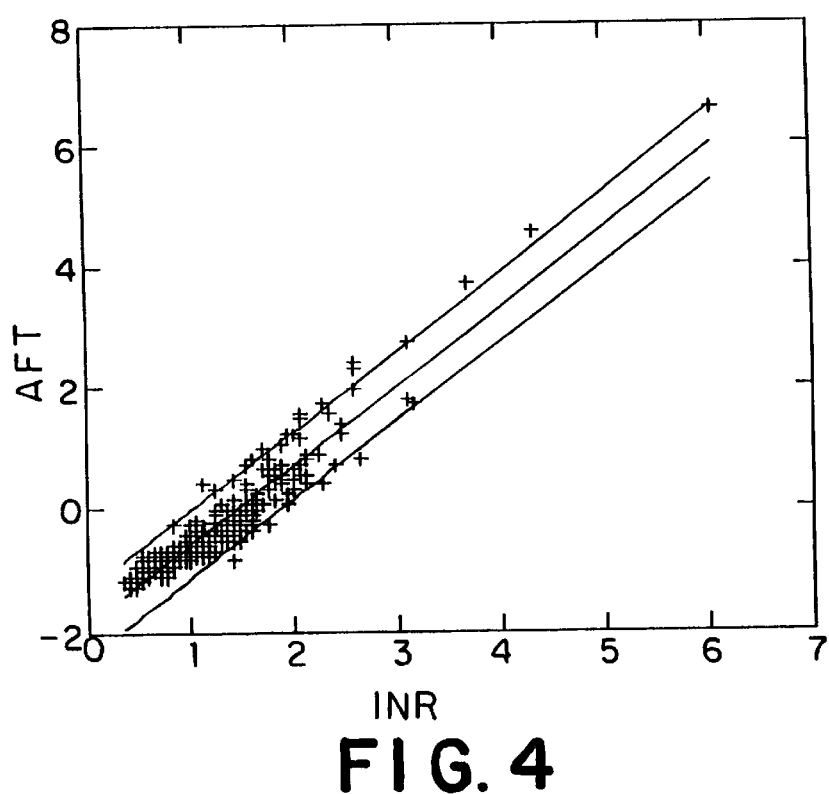
Figure 5:
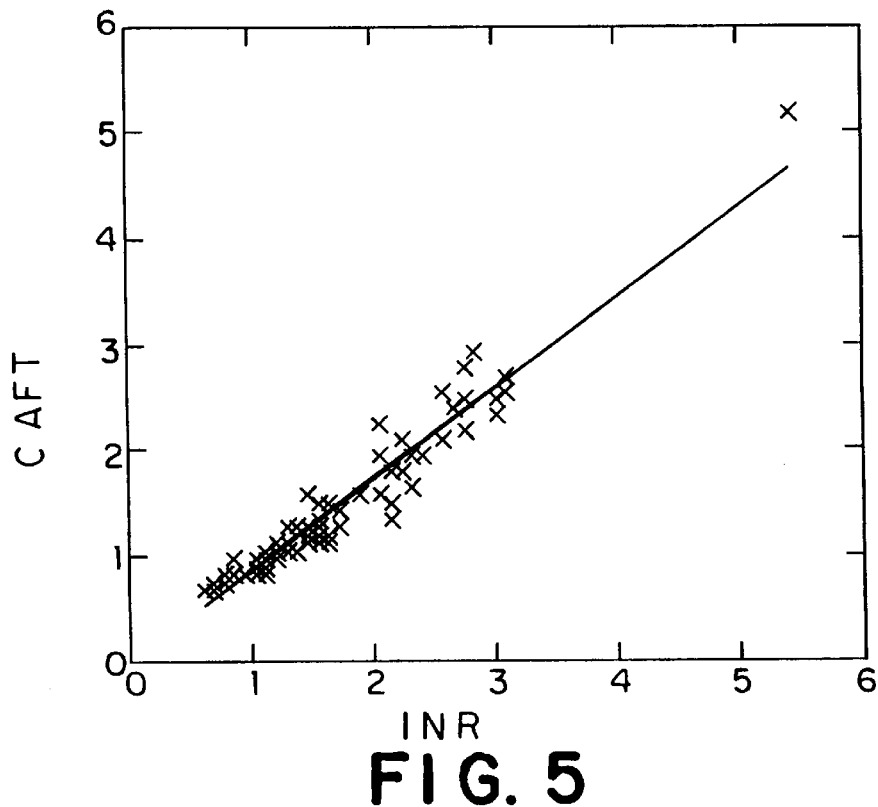
FIGS. 5, 6, 7 and 8 illustrate the correlation between the International Normalized Ratio (INR) and the corrected anticoagulant therapy factor (CATF) independently computed for three different thromboplastins.
Figure 6:
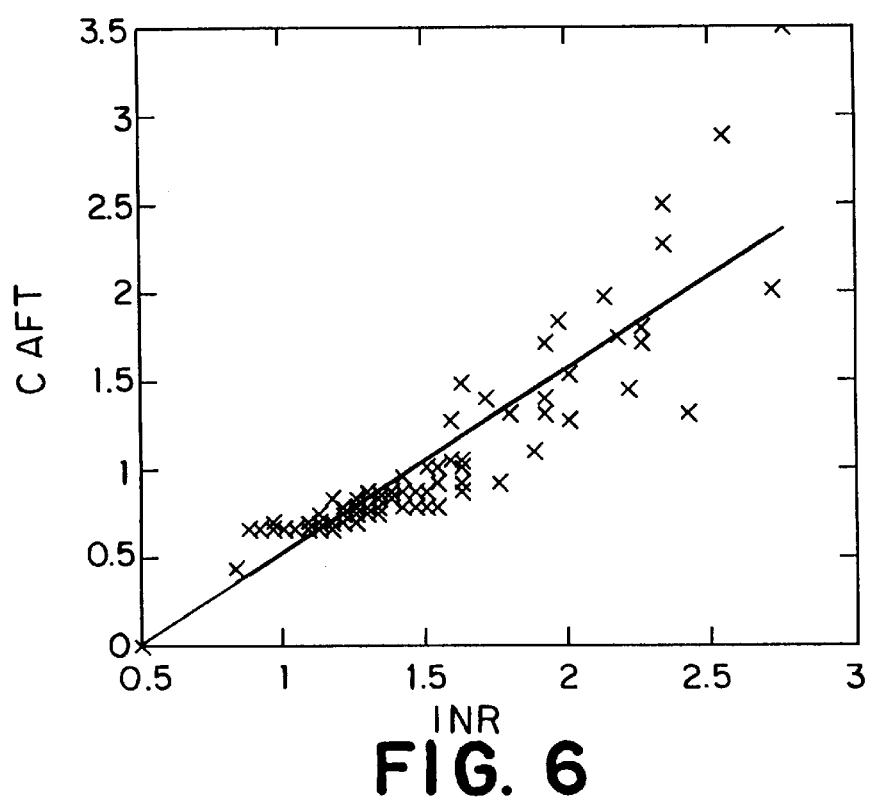
Figure 7:
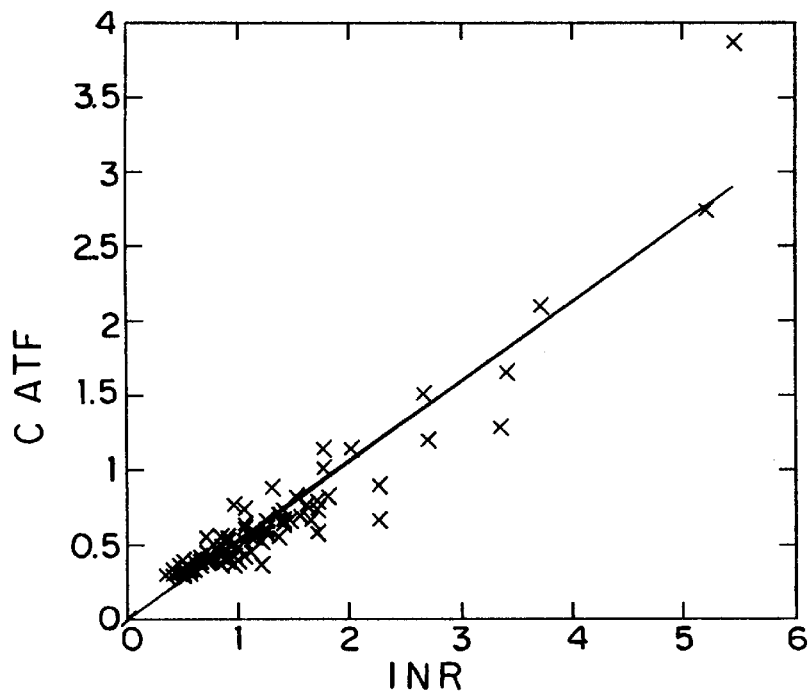

FIGS. 3 and 4 illustrate comparative testing showing the International Normalized Ratio (INR) of all Trays (I, II, III and IV) as the X axis, and the anticoagulant therapy factor (ATF) of all Trays (I, II, III and IV) as the Y axis. FIG. 3 illustrates the fibrinogen transformation rate (FTR) of a range of + and −0.5 seconds relative to the maximum acceleration point (MAP), whereas FIG. 4 illustrates a fibrinogen transformation rate (FTR) having a range of 1 second prior to the maximum acceleration point (MAP). The correlation obtained by the use of a +/−0.5 seconds fibrinogen transformation rate (FTR) range of FIG. 3 is 0.9334, which is better than the correlation of 0.9235 obtained from that of FIG. 4 using a fibrinogen transformation rate (FTR) range of −1.0 seconds.

Figure 8:
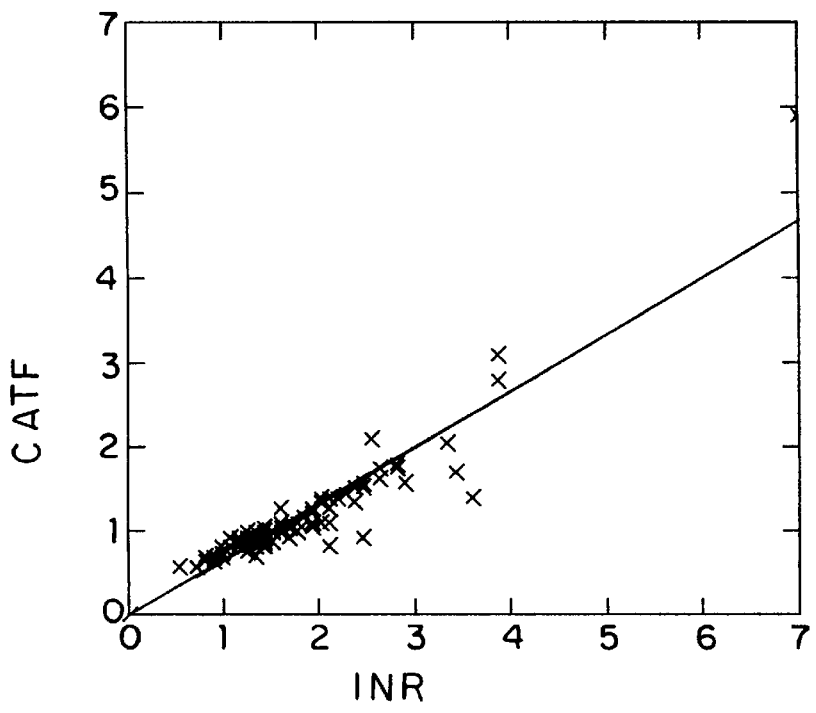

FIGS. 5, 6, 7 and 8 show the results of separately computing the International Normalized Ratio (INR) for Tray I (FIG. 5), Tray II (FIG. 6), Tray III (FIG. 7) and Tray IV (FIG. 8). FIGS. 5, 6, 7 and 8 respectively illustrate correlations of 0.948, 0.9632, 0.966, and 0.9653.

Although the hereinbefore description of anticoagulant therapy factor (ATF) does correlate well with the International Normalized Ratio (INR) when most of the patients being sampled were using a particular therapy, such as the anticoagulant Coumadin (previously discussed), it does suffer discrepancies when the ATF and INR quantities are compared for individual patients. These discrepancies are resolved when the anticoagulant therapy factor is statistically corrected, hereinafter referred to as corrected anticoagulant therapy factor (CATF), by the below expression (4):

$$CATF = PT*PR/FTR*(TMA/100) \qquad (4)$$

where the prothrombin ratio, PR, as used herein, =PT/MNPT, and the mean normal prothrombin time (MNPT), as used herein, is the geometric mean of the prothrombin time (PT) from at least 20 normal patients. The usage of the prothrombin ratio, PR, quantity in expression (4) more evenly spreads out the values of the prothrombin time, PT, quantity so as to yield a more sensitive CATF quantity of expression (4) as compared to the sensitivity of the ATF quantity of expression (2).

In general, it is desired to "correct" the ATF of expression (2) to be that of expression (4), so that the corrected anticoagulant therapy factor (CATF) corresponds as well as possible to the INR numerically. To visually show the correlation, the graphs (FIGS. 9–12, to be described) of INR vs ATF are mathematically manipulated so the slope of the plots of FIGS. 9–12 is one (1) and so that the linear repression line represented by these plots passes through the origin, that is, yields a zero (0) intercept line. These manipulations modify the values of ATF of expression (2) so that the CATF quantities of expression (4) almost equals INR. In general, to achieve the modified ATF (MATF) value to compare with the INR value, we compute the MEAN(X), MEAN(Y) and the SLOPE(X,Y) of all samples for each thromboplastin used, then make the geometric modifications in a manner to be described with reference to FIGS. 13–18 and, wherein the quantity MATF may be generally expressed by expression (5) given as follows:

$$\text{MATF}=((\text{CATF}-\text{MEAN}(Y))/\text{SLOPE}(XY))+\text{MEAN}(X) \qquad (5)$$

Figure 12:
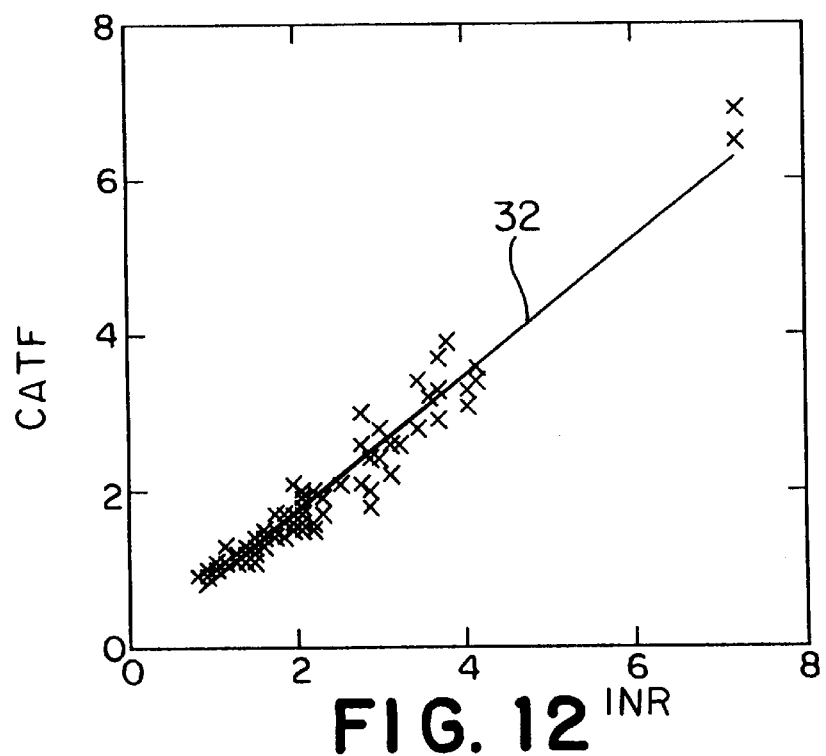
Figure 13:
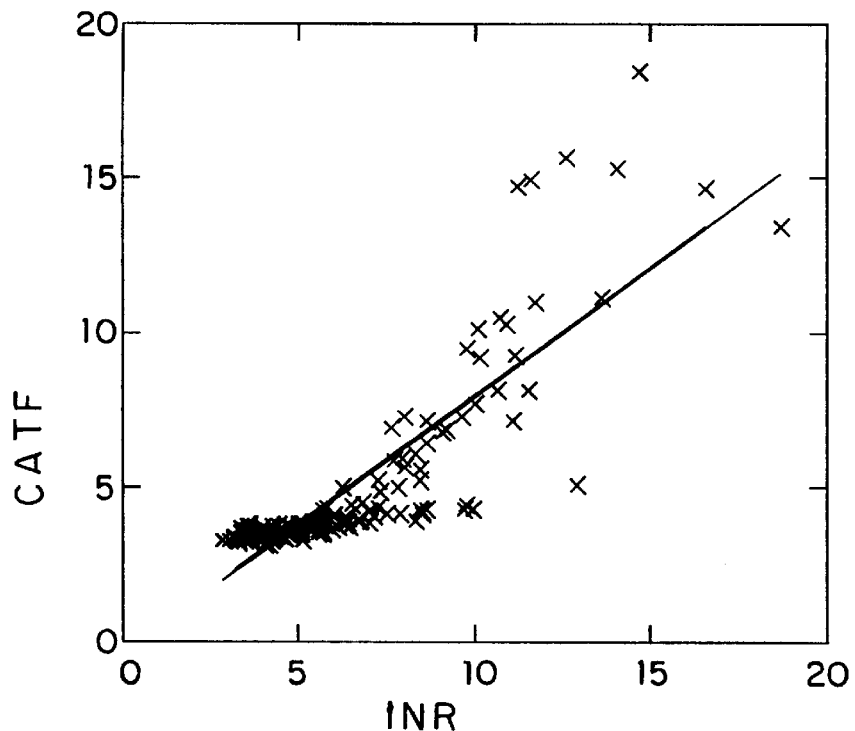
FIGS. 13 and 14 illustrate the correlation between the International Normalized Ratio (INR) and the corrected anticoagulant therapy factor (CATF) related to the present invention.
Figure 14:
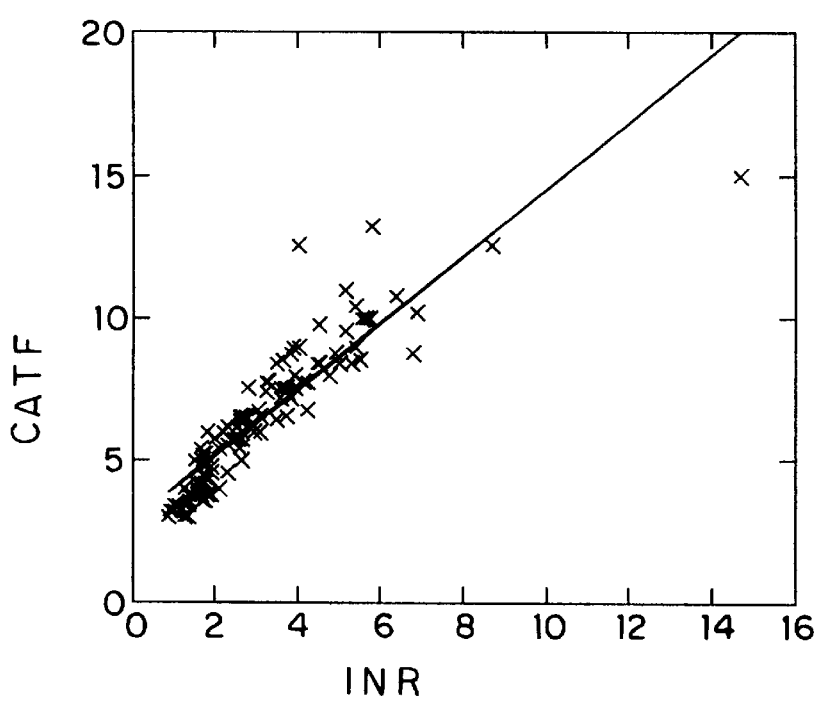
Figure 15:
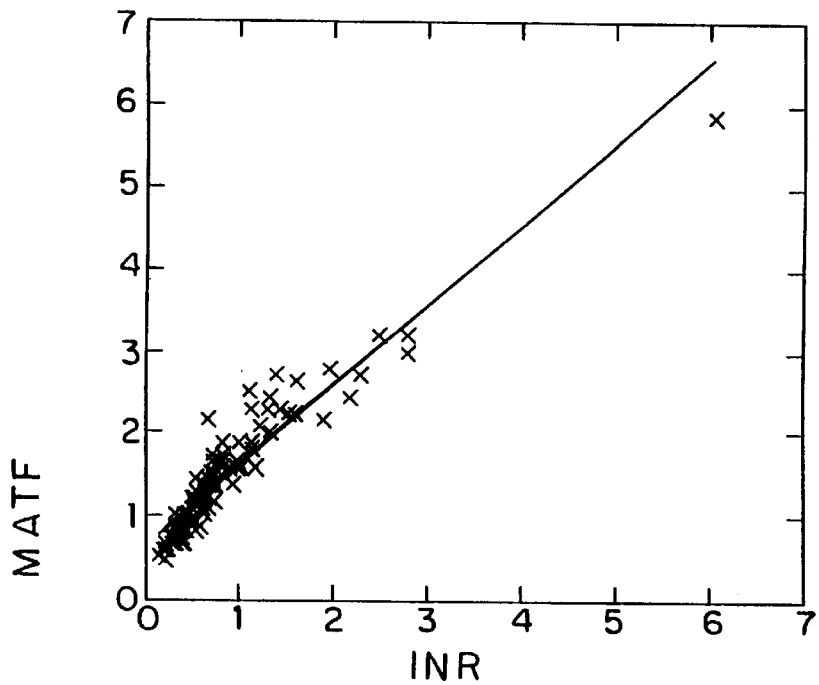
FIGS. 15, 16, 17, and 18 illustrate the correlation between the International Normalized Ratio (INR) and the modified anticoagulant therapy factor (MATF) related to the present invention.
Figure 16:
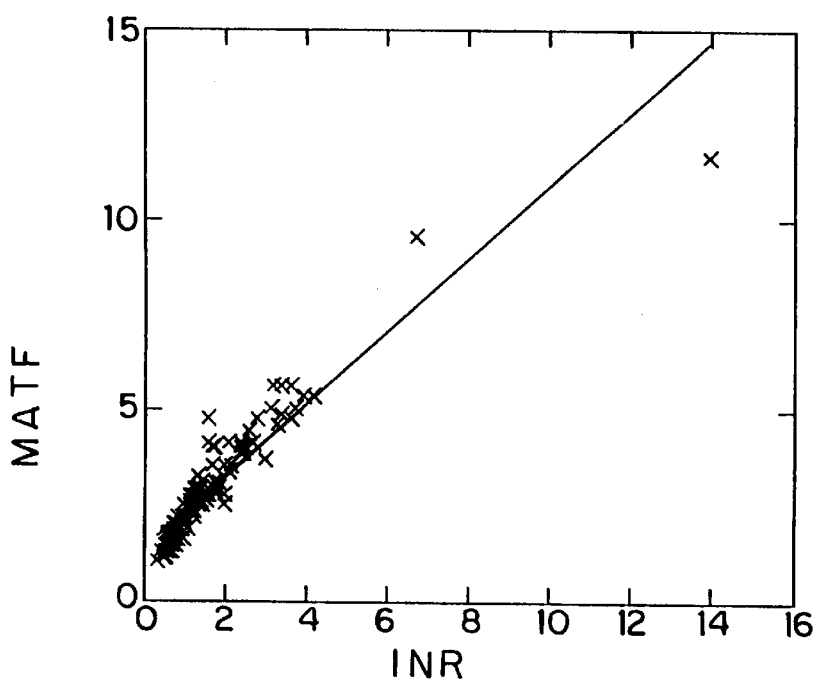
Figure 17:
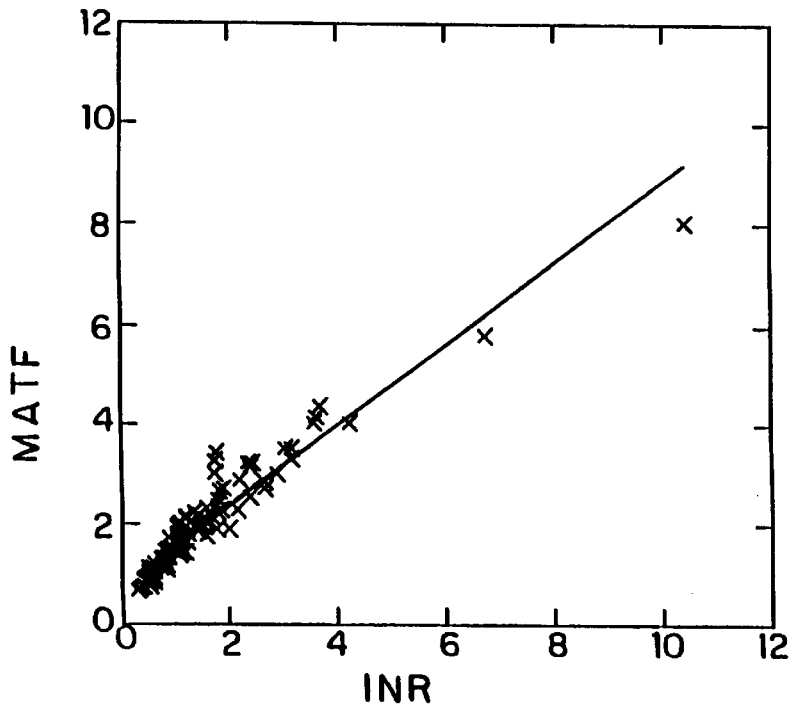
Figure 18:
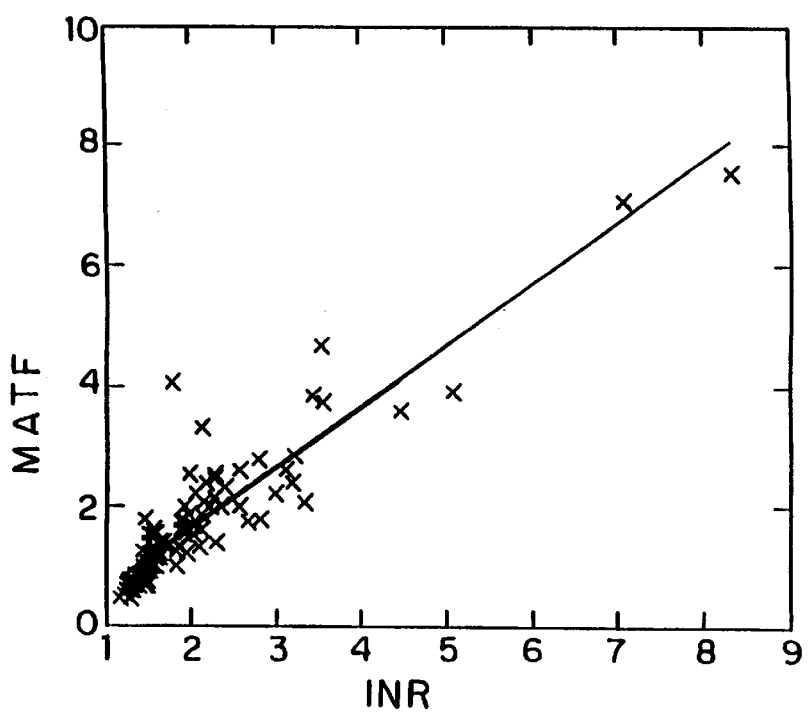

The correlation between CATF and INR is shown in FIGS. 13–14, to be further described, wherein the quantities X (INR) are those shown along the X axis, and the quantities Y (CATF) are those shown along the Y axis. To transform the quantities of expression (2) to those of expression (4), the following five (5) manipulations represented by the corresponding expressions (6)–(10) are accomplished with the X quantities thereof representing the INR quantities of FIGS. 9–12 and the Y quantities thereof representing the CATF quantities of FIGS. 13–14:

the mean of $X$, ($\bar{x}$) is derived with $\bar{x}$ also being referred to herein as mean $(x)$; \hfill (6)

the mean of $Y$, ($\bar{y}$) is derived with $\bar{y}$ also being referred to herein as mean $(y)$; \hfill (7)

then $X$ is set $= X - \bar{x}$, \hfill (8)

$Y$ is set $= Y - \bar{y}$ and the $Y$ is set $= \dfrac{y - \bar{y}}{\text{slope }(\bar{x}, \bar{y})}$;

Expressions (6), (7) and (8) makes the slope of the plots of FIGS. 9–14 equal to one (1) without altering the correlation of expression (2) related to INR; and \hfill (9)

the regression line still needs to be positioned for the intercept line to be zero (0) and to accomplish this $\bar{x}$ is added to $X$ and $Y$. \hfill (10)

The correlation between CATF and the INR quantities, in particular, the manipulation of collected data so as to provide plots with slopes of one (1) and with a zero (0) intercept may be described in a graphic manner with reference to FIGS. 9–12.

Figure 9:
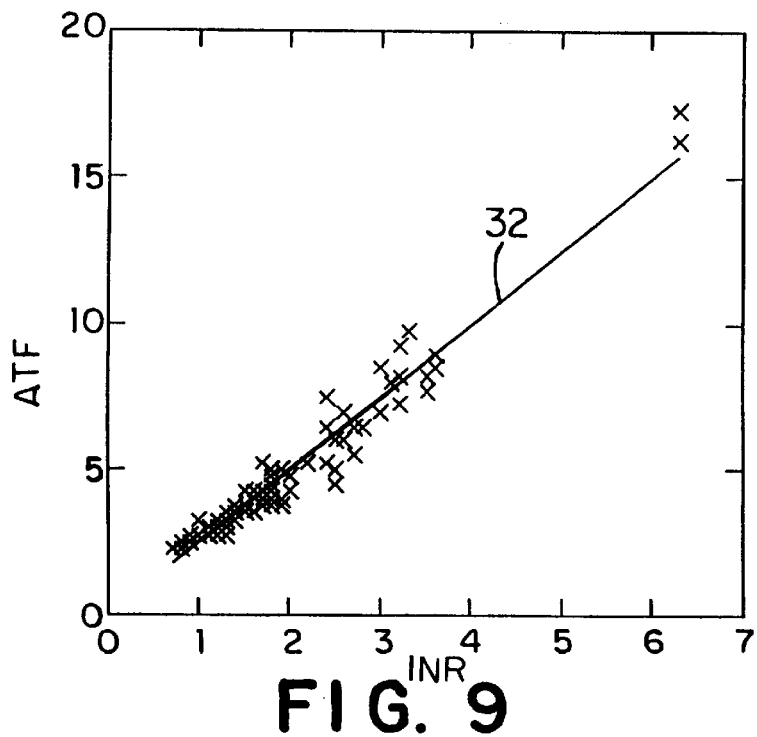
FIGS. 9, 10, 11 and 12 graphically illustrate, in accordance with the practice of the present invention, the transition of a plot (FIG. 9) not having a slope of one (1) nor an intercept of zero (0), to a plot (FIG. 12) having both a slope of one (1) and an intercept of zero (0).

FIG. 9 illustrates a plot 32 for various collected data (generally indicated with X symbols) from 92 samples, wherein the data associated with the X and Y axes having a correlation factor, r, of 0.9759. The slope of the plot 32 of FIG. 9 is 2.8388 and the intercept is −1.6852. As previously discussed, it is desired by the practice of this invention to maintain the quality of the data defined by plot 32 but to change the slope to one (1) and the intercept to zero (0).

Figure 10:
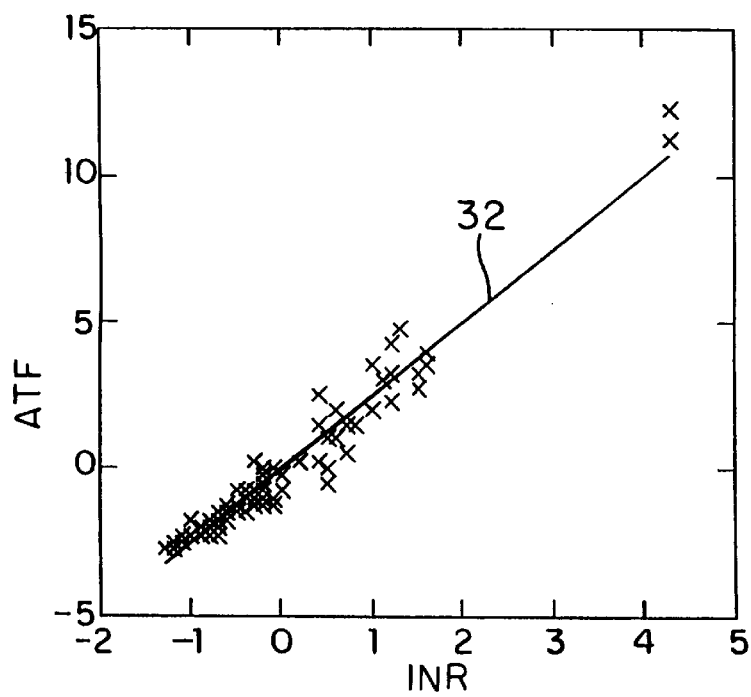

FIG. 10 illustrates the plot 32 as having an intercept of zero (0) and this is accomplished by setting X=x−mean(x) and Y=y−mean(y), where the quantities x and y are the data of FIG. 9. A comparison between the X and Y axes of FIGS. 9 and 10 reveals that the values of the Y axis are changed from 0 to 20 of FIG. 9 to −5 to 15 of FIG. 10 and, similarly, the values of the X axis are changed from 0 to 7 of FIG. 9 to −2 to 5 of FIG. 10. However, the distribution and correction factor, r, of plot 32 remain the same.

Figure 11:
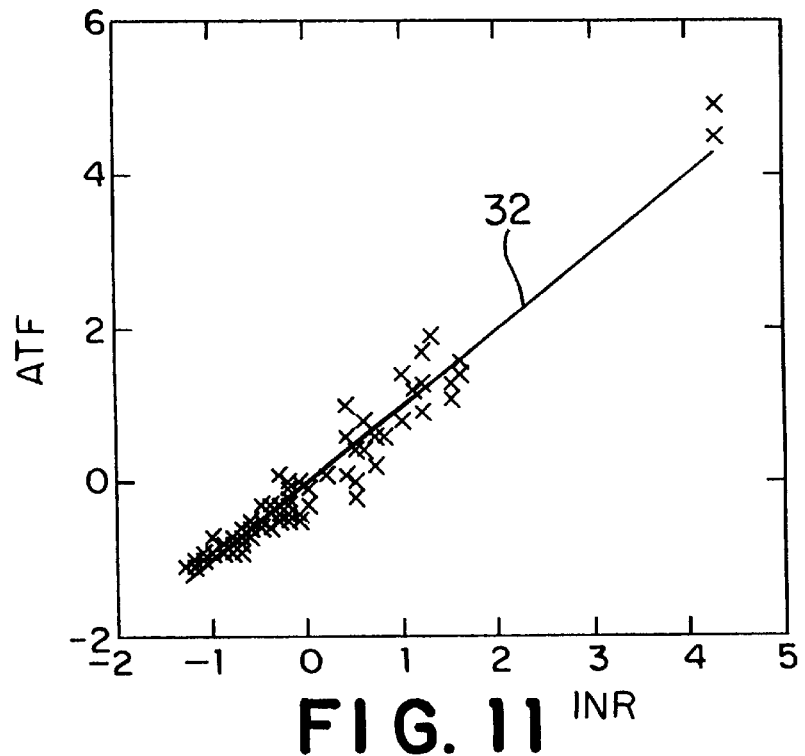

FIG. 11 illustrates the plot 32 as having a slope of one (1) and this is accomplished by setting X=to the x quantities of FIG. 10 and Y=to the y quantities of FIG. 10 and then setting Y=Y/Slope (x, y) with x,y being the quantities of FIG. 9. A comparison between the X and Y axes of FIGS. 10 and 11 reveals that the values of the Y axis are changed from −5 to 15 of FIG. 10 to −2 to 6 of FIG. 11 and, conversely, the values of the X axis for both FIGS. 10 and 11 remain the same; i.e., −2 to 5.

FIG. 12 illustrates the plot 32 as having an intercept line of zero (0) and this is accomplished by setting X and Y to the quantities of FIG. 11 and then setting X=Y+ mean(x) and Y=Y+ mean(x), with x and y being the quantities of FIG. 9. A comparison between the X and Y axes of FIGS. 11 and 12 reveals that the values of Y axis are changed from −2 to 6 of FIG. 11 to 0 to 8 of FIG. 12 and, similarly, the values of the X axis are changed from −2 to 5 of FIG. 11 to 0 to 8 of FIG. 12. More importantly, the values defining the X and Y axes are the same; i.e., 0 to 8.

FIG. 12 having a plot 32 with a slope (1) and a zero (0) intercept line provides data comprised of x and y points having values defined by the practice of this invention for the INRs quantities and CATFs quantities of expression (4) that agree with The computer 30 may be used to manipulate and derive the quantities of expression (4) utilizing known programming routines and techniques. The data collected by an computer 30 used to manipulate and derive the anticoagulant therapy factor (ATF) of expression (2) may be used and becomes the same data that is used to manipulate and derive the corrected anticoagulant therapy factor (CATF) of expression (4). Similarly, one skilled in the art, using known mathematical techniques may derive the prothrombin ratio (PR) and the mean normal prothrombin time (MNPT) of expression (4) which, in turn, are used to determine the corrected anticoagulant therapy (CATF) of expression (4). The accuracy of these quantities is dependent, in part, on the number of specimens used, that is, the number of stable patients; wherein for the practice of the present invention, to be further discussed hereinafter with reference to a calibration procedure, a number of at least twenty (20) of stable patients is preferably used and which is in agreement with that used in the art to establish a population sampling standard, such as disclosed in the previously incorporated by reference technical article of L. Poller et al.

The greater than twenty (20) specimens each are separately handled to derive separate corrected anticoagulant therapy factor (CATF), but with a plurality of specimens being manipulated to derive the mean normal prothrombin time (MNPT) that is used in the derivation of each separate anticoagulant therapy factor (CATF) quantity.

Conwarative Testing of CATF and INR Ouantities

In the practice of the invention, the INRs, ATFs and corrected ATFs (CATF of expression (4)) were determined from 20 normal patients. Quantities of ATF and INR used in the practice were already available, such as those discussed with reference to FIGS. 2–8. Further, additional INR, were determined using a thromboplastin, Thromboplastin C plus of the Dade Corporation, which was analyzed by using a Coag-A-Mate Coagulation Analyzer known in the art. The INRs determined by the Coag-A-Mate Coagulation Analyzer were compared to corrected AFTs. The comparison between the corrected ATFs and gathered INRs may be further described with reference to FIG. 13 previously mentioned.

FIGS. 13 and 14 are similar to FIGS. 3–4 having a X axis indicated by INR, but now having a Y axis indicated by CATF. FIG. 13 shows the composite plot of corrected AFTs (CATF) versus INRs for 510 samples from the stable patients using four separate thromboplastins; Thromboplastin C plus (TPC), Innovin (INN), Sigma (SIG) and Pacific Hemostasis-D (PHT) all known in the art. The plot of FIG. 13 has a correlation factor r, =0.6860. From FIG. 13, in a manner as previously discussed, it should be noted that the plot thereof represents a zero (0) intercept line and has a slope of 1 both previously described. The comparison between the corrected ATFs (CATF) and INR related to the present invention may be further described with reference to FIG. 14.

FIG. 14 shows the plot of corrected ATFs (CATF) versus INR for 380 samples from the 20 stable patients yielding a correlation factor, r, of 0.9126. FIG. 14 differs from FIG. 13 in that the INN thromboplastin of FIG. 13 was excluded from FIG. 14.

As in known in the art, the INN thromboplastin is prepared by recombinant technology and has an ISI of 1.02, whereas the other three thromboplastins (TPC, SIG and PHT) are prepared from rabbit brain and have ISIs of 2.12, 2.51 and 1.99 respectively. The use of INN thromboplastin results in definitely longer prothrombin times in otherwise prolonged specimens (i.e., times greater than 15 seconds) and the INN thromboplastins also has a slower reacting time as may be seen in the clotting graphs of time vs optical density yielded by using the arrangement of FIG. 1. This slower reaction time results in individual tests ending before the actual final total fibrinogen (FBG) value is achieved. A small number for FBG results, so the FTR is increased and the ATF, hereby, increases. (This end point detection problem also exists to a lesser extent with Sigma thromboplastin). The problem can be resolved by extending measurement time until "End of Test" results or 120 second expire, whichever comes first. The error at 120 sec does not matter, as compared to tests that run with a cut-off time of 60 seconds. The 60 second duration is fully adequate for prothrombin times; but not, as is apparent, for FBGs determined using INN and to a lesser extent using the SIG thromboplastin. The comparison testing between the modified ATFs (MATF) and INR's may be further described with reference to FIGS. 15–18.

FIGS. 15, 16, 17 and 18 illustrate the plots showing the correlation between the modified anticoagulant therapy factor (MATFs) and the INR's respectively using 92 samples derived from the TPC thromboplastin yielding a correlation factor, r, of 0.9759; 93 samples derived from the SIG thromboplastin yielding a correlation factor, r, of 0.9442; 101 samples derived from the PHT thromboplastin yielding a correlation factor, r, of 0.9268; and 96 samples of the INN thromboplastin yielding a correlation factor, r, of 0.8927.

A review of the above results illustrated in FIGS. 13–14 show an acceptable correlation factor (r) of corrected ATFs (CATFs) to INRs, and a review of the above results illustrated in FIGS. 15–18 show an acceptable correlation factor (r) of modified ATFs (MATFs) to INRS. The results are further improved when INN thromboplastin (included in FIGS. 13 and 15) is excluded, but clinical medicine demands attention to the individual patient. Accordingly, the use of the INN thromboplastin needs to be taken into account. In this part of the study shown in FIGS. 13–18, we compared corrected ATFs (CATFs) and modified ATFs (MATFS) to the INRs determined on the "POTENS +" arrangement of FIG. 1 and/or in the clinical laboratory by using the Coag-A-Mate Coagulation Analyzer known in the art. These clinical laboratory INR results were those actually used for patient care in a manner as hereinbefore described. The raw data accumulated to derive the plots of FIGS. 15–18 are given below in Tables 2 and 3.

TABLE 2

| TPC | | INN | | SIG | | PHT | |
|---|---|---|---|---|---|---|---|
| INR's | MATF's | INR's | MATF's | INR's | MATF's | INR's | MATF's |
| 3.6 | 3.6 | 1.5 | 1.5 | 4.0 | 4.3 | 3.2 | 3.1 |
| 1.2 | 1.1 | 1.0 | 1.5 | 1.1 | 1.2 | 1.4 | 1.3 |
| 0.8 | 0.9 | 2.4 | 2.0 | 0.9 | 1.2 | 0.9 | 1.1 |
| 1.7 | 1.5 | 1.0 | 1.5 | 2.4 | 2.0 | 1.8 | 1.7 |
| 0.9 | 1.0 | 1.4 | 1.5 | 0.8 | 1.3 | 1.0 | 1.2 |
| 1.2 | 1.2 | 3.4 | 3.0 | 1.0 | 1.2 | 1.1 | 1.2 |
| 3.2 | 3.7 | 2.1 | 1.9 | 3.1 | 2.6 | 2.9 | 3.6 |
| 1.9 | 1.6 | 4.4 | 5.2 | 3.4 | 2.2 | 2.2 | 2.1 |
| 3.0 | 2.8 | 2.7 | 2.4 | 2.5 | 2.2 | 2.3 | 1.9 |
| 2.4 | 2.1 | 2.7 | 2.1 | 2.2 | 2.1 | 2.2 | 1.8 |
| 1.3 | 1.4 | 2.2 | 2.0 | 1.2 | 1.5 | 2.4 | 1.9 |
| 1.4 | 1.3 | 1.6 | 1.5 | 1.7 | 1.6 | 1.3 | 1.4 |
| 1.8 | 1.6 | 2.0 | 1.8 | 1.6 | 1.5 | 1.6 | 1.4 |
| 1.9 | 1.5 | 2.0 | 1.8 | 1.3 | 1.5 | 1.6 | 1.7 |
| 3.0 | 3.4 | 1.8 | 1.8 | 1.7 | 1.4 | 1.3 | 1.4 |
| 1.0 | 1.1 | 2.2 | 1.8 | 6.7 | 4.8 | 1.7 | 1.5 |
| 3.5 | 3.1 | 4.4 | 5.7 | 1.1 | 1.3 | 4.4 | 4.8 |
| 3.2 | 2.9 | 1.3 | 1.5 | 3.4 | 2.8 | 1.2 | 1.4 |
| 2.5 | 2.4 | 4.2 | 4.1 | 5.4 | 4.5 | 3.2 | 3.0 |
| 1.7 | 1.6 | 5.3 | 4.6 | 1.8 | 1.5 | 4.4 | 5.3 |
| 1.3 | 1.1 | 2.3 | 1.8 | 1.3 | 1.5 | 2.4 | 2.2 |
| 1.9 | 2.0 | 1.5 | 1.5 | 2.4 | 1.4 | 1.8 | 2.2 |
| 1.2 | 1.1 | 3.0 | 2.1 | 1.5 | 1.6 | 1.6 | 1.5 |
| 1.3 | 1.2 | 1.9 | 1.7 | 1.5 | 1.5 | 2.1 | 2.0 |
| 0.7 | 0.9 | 1.6 | 1.6 | 0.8 | 1.1 | 1.5 | 1.6 |
| 3.2 | 3.3 | 1.1 | 1.5 | 3.3 | 2.5 | 1.6 | 1.6 |
| 2.5 | 1.8 | 3.6 | 2.9 | 4.5 | 2.5 | 0.8 | 1.0 |
| 2.0 | 1.7 | 4.6 | 3.0 | 2.0 | 1.5 | 3.3 | 2.7 |
| 0.8 | 1.0 | 2.4 | 1.8 | 1.0 | 1.5 | 4.1 | 2.4 |
| 0.9 | 1.0 | 1.0 | 1.5 | 0.9 | 1.4 | 2.2 | 1.9 |
| 1.6 | 1.7 | 2.7 | 2.0 | 2.5 | 2.3 | 0.9 | 1.1 |
| 1.7 | 1.6 | 1.9 | 1.7 | 1.6 | 1.7 | 1.1 | 1.3 |
| 1.3 | 1.3 | 1.5 | 1.6 | 1.3 | 1.4 | 2.3 | 2.4 |
| 2.7 | 2.6 | 3.4 | 3.2 | 2.1 | 2.4 | 1.4 | 1.7 |
| 1.3 | 1.2 | 1.5 | 1.6 | 2.3 | 2.2 | 1.7 | 1.7 |
| 0.8 | 0.9 | 1.0 | 1.5 | 1.1 | 1.3 | 1.4 | 1.4 |
| 1.2 | 1.2 | 4.0 | 4.0 | 0.7 | 1.1 | 2.0 | 1.9 |
| 2.6 | 2.4 | 1.5 | 1.7 | 5.3 | 5.7 | 2.2 | 2.2 |
| 2.4 | 2.6 | 1.7 | 1.8 | 1.4 | 2.1 | 1.3 | 1.4 |

TABLE 2-continued

| TPC | | INN | | SIG | | PHT | |
|---|---|---|---|---|---|---|---|
| INR's | MATF's | INR's | MATF's | INR's | MATF's | INR's | MATF's |
| 2.5 | 2.0 | 3.3 | 2.5 | 3.5 | 3.8 | 0.8 | 1.0 |
| 1.4 | 1.5 | 2.7 | 3.4 | 2.6 | 3.3 | 1.1 | 1.3 |
| 1.6 | 1.4 | 2.9 | 3.2 | 2.7 | 2.7 | 1.4 | 1.6 |
| 1.2 | 1.3 | 2.0 | 1.9 | 1.3 | 1.5 | 2.3 | 2.3 |
| 2.0 | 1.9 | 1.7 | 1.6 | 1.9 | 2.9 | 2.4 | 2.4 |
| 3.6 | 3.4 | 1.7 | 1.7 | 3.5 | 4.3 | 1.6 | 1.4 |
| 1.0 | 1.3 | 4.9 | 6.6 | 7.4 | 7.9 | 1.4 | 1.4 |
| 1.6 | 1.7 | 1.9 | 2.0 | 1.3 | 1.6 | 1.4 | 1.5 |
| 1.5 | 1.5 | 2.3 | 2.0 | 2.1 | 2.0 | 2.7 | 2.6 |
| 1.8 | 2.0 | 1.4 | 1.6 | 1.4 | 1.7 | 3.9 | 2.9 |
| 1.8 | 1.9 | 1.9 | 1.8 | 1.6 | 1.7 | 1.3 | 1.5 |
| 6.3 | 6.5 | 2.2 | 2.2 | 2.1 | 2.3 | 1.8 | 1.9 |
| 1.1 | 1.2 | 1.6 | 1.6 | 2.1 | 2.8 | 1.3 | 1.6 |
| 6.3 | 6.9 | 4.1 | 3.3 | 1.4 | 1.5 | 1.5 | 1.5 |
| 1.3 | 1.2 | 1.9 | 1.8 | 11.0 | 15.0 | 2.0 | 1.9 |
| 2.6 | 2.4 | 2.0 | 1.7 | 3.6 | 3.1 | 1.9 | 1.8 |
| 1.2 | 1.2 | 1.8 | 1.9 | 1.8 | 2.1 | 1.1 | 1.4 |
| 0.8 | 0.9 | 3.1 | 3.0 | 6.8 | 6.2 | 2.8 | 1.6 |
| 1.8 | 1.8 | 1.2 | 1.5 | 1.9 | 1.6 | 1.9 | 1.6 |
| 1.8 | 1.7 | 2.1 | 2.0 | 1.9 | 1.4 | 1.5 | 1.2 |
| 0.8 | 0.9 | 2.0 | 2.0 | 2.2 | 1.7 | 3.0 | 3.0 |
| 0.9 | 1.0 | 1.2 | 1.5 | 1.0 | 1.5 | 1.5 | 1.7 |
| 1.5 | 1.4 | 1.1 | 1.5 | 1.0 | 1.3 | 2.8 | 2.6 |
| 0.7 | 0.9 | 1.9 | 1.7 | 1.4 | 1.5 | 0.9 | 1.2 |
| 1.8 | 1.6 | 0.9 | 1.5 | 1.7 | 1.9 | 2.0 | 1.7 |
| 2.2 | 2.1 | 2.0 | 1.7 | 2.8 | 2.8 | 2.2 | 1.8 |
| 1.5 | 1.5 | 2.6 | 2.9 | 4.5 | 3.4 | 1.0 | 1.2 |
| 1.6 | 1.4 | 3.5 | 4.2 | 1.7 | 2.1 | 0.9 | 1.1 |
| 1.7 | 1.5 | 1.6 | 1.9 | 2.8 | 2.5 | 1.5 | 1.4 |
| 1.4 | 1.4 | 2.5 | 2.1 | 2.9 | 2.5 | 0.6 | 1.0 |
| 2.7 | 2.2 | 2.5 | 1.8 | 3.2 | 2.9 | 1.5 | 1.6 |
| 2.8 | 2.6 | 2.4 | 2.3 | 2.0 | 1.8 | 2.5 | 2.4 |
| 1.9 | 2.0 | 2.6 | 2.4 | 1.3 | 1.5 | 2.7 | 2.3 |
| 1.4 | 1.3 | 1.8 | 1.7 | 1.6 | 1.8 | 1.4 | 1.6 |
| 1.7 | 1.7 | 1.8 | 1.6 | 1.6 | 1.5 | 1.9 | 1.6 |
| 1.4 | 1.4 | 1.9 | 1.8 | 1.3 | 1.6 | 2.4 | 1.4 |
| 1.2 | 1.3 | 1.8 | 1.7 | 2.3 | 2.1 | 2.2 | 2.1 |
| 2.6 | 2.8 | 1.3 | 1.5 | 3.0 | 3.1 | 1.1 | 1.6 |
| 2.4 | 3.0 | 3.1 | 2.6 | 1.8 | 2.0 | 1.2 | 1.6 |
| 0.9 | 1.1 | 3.4 | 3.9 | 1.0 | 1.2 | 1.5 | 1.5 |
| 1.8 | 1.5 | 2.2 | 2.0 | 2.1 | 1.6 | 1.6 | 1.8 |
| 1.5 | 1.5 | 1.3 | 1.5 | 1.8 | 1.6 | 1.6 | 1.5 |
| 1.1 | 1.1 | 2.6 | 2.0 | 1.5 | 1.5 | 1.4 | 1.5 |
| 0.9 | 1.1 | 2.0 | 1.8 | 1.0 | 1.1 | 2.2 | 2.5 |
| 1.5 | 1.7 | 1.8 | 1.7 | 1.6 | 1.7 | 3.0 | 2.8 |
| 3.1 | 3.2 | 1.3 | 1.5 | 2.8 | 2.4 | 1.7 | 1.8 |
| 3.3 | 3.9 | 1.2 | 1.5 | 0.9 | 1.2 | 1.0 | 1.1 |
| 0.8 | 1.0 | 4.2 | 3.9 | 2.7 | 2.1 | 2.0 | 1.7 |
| 1.7 | 2.1 | 3.9 | 4.5 | 10.0 | 10.0 | 1.8 | 1.8 |
| 1.1 | 1.1 | 1.1 | 1.5 | 2.5 | 2.5 | 1.6 | 1.6 |
| 3.5 | 3.3 | 2.5 | 2.3 | 1.0 | 1.2 | 1.1 | 1.2 |
| 1.0 | 1.1 | 2.7 | 2.3 | 3.4 | 3.0 | 0.9 | 1.2 |
| 0.8 | 1.0 | 1.5 | 1.5 | 1.2 | 1.3 | 1.4 | 1.7 |
| | | 3.6 | 3.5 | 0.7 | 1.1 | 3.8 | 3.5 |
| | | 5.4 | 8.0 | | | 0.9 | 1.2 |
| | | 1.4 | 1.6 | | | 2.6 | 2.5 |
| | | 1.0 | 1.5 | | | 8.0 | 10.0 |
| | | | | | | 2.0 | 1.9 |
| | | | | | | 1.1 | 1.2 |
| | | | | | | 2.8 | 2.7 |
| | | | | | | 1.1 | 1.3 |
| | | | | | | 0.8 | 1.0 |

TABLE 3

| Clinical Lab INR | MATF'S |
|---|---|
| 1.6 | 1.4 |
| 2.2 | 1.8 |
| 1.4 | 1.5 |
| 2.3 | 2.1 |
| 3.9 | 3.7 |
| 1.4 | 1.4 |

TABLE 3-continued

| Clinical Lab INR | MATF'S |
|---|---|
| 1.8 | 1.4 |
| 1.0 | 1.3 |
| 1.1 | 1.3 |
| 2.1 | 2.0 |
| 1.2 | 1.2 |
| 1.2 | 1.3 |
| 2.9 | 2.7 |
| 1.8 | 1.7 |
| 2.2 | 2.0 |
| 1.3 | 1.3 |
| 2.4 | 1.9 |
| 2.7 | 2.0 |
| 1.3 | 1.3 |
| 2.1 | 2.0 |
| 3.3 | 3.0 |
| 1.1 | 1.2 |
| 1.5 | 1.4 |
| 3.4 | 2.9 |
| 2.1 | 1.8 |
| 2.0 | 1.7 |
| 1.2 | 1.3 |
| 2.3 | 1.9 |
| 2.3 | 1.7 |
| 3.0 | 2.9 |
| 1.9 | 1.6 |
| 4.0 | 4.0 |
| 2.2 | 2.0 |
| 2.1 | 1.8 |
| 2.3 | 2.2 |
| 1.8 | 1.5 |
| 1.3 | 1.2 |
| 2.4 | 2.0 |
| 1.3 | 1.3 |
| 1.0 | 1.2 |
| 2.8 | 2.6 |
| 1.9 | 1.9 |
| 1.9 | 2.4 |
| 1.7 | 1.7 |
| 1.3 | 1.4 |
| 1.4 | 1.4 |
| 1.3 | 1.4 |
| 2.0 | 2.1 |
| 3.9 | 3.8 |
| 4.2 | 4.5 |
| 2.6 | 2.6 |
| 1.6 | 1.4 |
| 1.6 | 1.4 |
| 1.2 | 1.3 |
| 2.2 | 1.7 |
| 2.4 | 2.1 |
| 1.9 | 1.8 |

Table 2 has four (4) columns grouped into TPC thromboplastin, INN thromboplastin, SIG thromboplastin and PHT thromboplastin, each of which is sub-divided into two columns INR's and MATF's. Table 3 has two columns respectively identified as clinical Lab INR and modified ATFs (MATF's). In each of the columns of Tables 2 and 3 the quantities therein are considered to be undesired if the individual MATFs differs from the corresponding mean INR by more than ±10%. Further, in each of the columns of Tables 2 and 3 the quantities therein are considered undesired if the individual MATF is within * ±10% of the corresponding INR for a given range of INR, such as International Sensitivity Index (sui) of between 2–3.0, but outside of ±10% range of the corresponding INR for a different range of INR, such as ISI of between 3.0–4.5.

Table 2 shows four columns of pairs of data, representing MATF values vs INRs with the MATF being obtained from the "POTENS +" arrangement of FIG. 1. The MATF in each column is related to its own paired INR, and each of the four paired columns is independent of the others. When comparing the obtained INR to the sample or standard INR acting as a reference, a difference of 0.5 units therebetween is considered acceptable. Also considered acceptable, is when the INR is within +/−10% of the corresponding mean sample INR value. When this same ruler is applied to the ATFs and INRs, 0.5 units or less is considered an acceptable difference, in a manner similar to that described in the Technical Bulletin, Judy R. Bodwell, MT (ASCP) SC, Boehringer Mannheim Corporation, herein incorporated by reference, or when the ATF is within + or −10% of INR reference in a manner similar to that disclosed in the previously mentioned reference of Poller et al, *American Journal of Clinical Pathology* 1998; 109; 196–204. The therapeutic range for INRs for treatment of venous thrombosis, pulmonary embolism, and prevention of systemic embolism is 2.0–3.0 and for mechanical prosthetic valves it is 2.5–3.5 units. The ranges of INR for various treatment are more fully disclosed in the technical article entitled "Mechanism of Action, Clinical Effectiveness, and Optimal Therapeutic Range" of J. Hirsh et al, published in *Oral Anticoagulants; Chest*, 102, Oct., 4, 1991, Supplement.

A review of Table 2 reveals, that for the use of the TPC thromboplastin two (2) patients out of ninety-two (92) showed a difference greater than 0.5 units.

A further review of Table 2 reveals that for the use of INN thromboplastin, 10 of 96 patients shows an MATF-INR difference greater than 0.5 and some adjustment in the INN thromboplastin dosage could be considered to bring patients back into range. For the use of the SIG thromboplastin, 12 of 93 patients had differences greater than 0.5 and some of these patients would probably not require medication change. For the use of the PHT thromboplastin, 5 of 101 patients showed a greater than 0.5 difference and some would probably not require a change in medication.

An overall review of Table 2 reveals good results for the individual patients with each of the four thromboplastins, especially with TPC and PHT thromboplastins and with less desired results for INN and SIG thromboplastins relative to those obtained from the TPC and PHT thromboplastins.

A review of Table 3 of the "modified ATFs" to the INRs determined in the clinical laboratory, for samples from 57 patients reveals only 1 patient exhibited a difference greater than 0.5 units. In the comparison of Table 2, TPC was used on both coagulation instruments, i.e., on the "POTENS +" arrangement of FIG. 1 and on the one available in the clinical laboratory, that is, the Coag-A-Mate system.

The information given in Tables 2 and 3 may be reformatted as shown in the below Tables 4A and 4B, respectively, and compared to the information and analysis described in the previously incorporated by reference technical article of V.L. NG et al, more particularly, Table 4 therein:

TABLE 4A

| Thrombo-plastin | RANGE | | | | Total Number of Mismatches |
|---|---|---|---|---|---|
| | <2.0 | 2.0–3.0 | >3.0–4.5 | >4.5 | |
| TPC | 4(4,0)/63 | 4(1,3)/17 | 1(0,1)/9 | 1(0,1)/3 | 10/92 = 11.0% |
| INN | 1(1,0)/45 | 13(2,11)/31 | 7(2,5)/16 | 1(0,1)/4 | 22/96 = 23.0% |
| SIG | 4(4,0)/50 | 7(2,5)/24 | 7(0,7)/12 | 1(0,1)/7 | 19/93 = 20.0% |
| PHT | 1(1,0)/62 | 13(1,12)/30 | 6(2,4)/8 | 0(0,0)/1 | 20/101 = 20.0% |

TABLE 4B

| Thrombo-plastin | <2.0 | RANGE 2.0–3.0 | >3.0–4.5 | >4.5 | Total Number of Mismatches |
|---|---|---|---|---|---|
| TPC | 1(1,0)/29 | 8(0,8)/22 | 2(0,2)/6 | 0(0,0)/0 | 11/57 = 19.0% |

Tables 4A and 4B are arranged in a similar manner as that of Table 4 of the technical article of V. L. NG et al, wherein the left-most column thereof indicates the Thromboplastin used, the central columns thereof indicate the therapeutic ranges, and the right-most column indicates the total number of mismatches. More particularly, and using the TPC thromnboplastin of range <2.0 of Table 4A as an example, the central columns indicate the total number (4) of lower and highs (0,4) reading of JNR in that particular range, and the total number (60) of samples taken in that particular range. Further for this same example, the right-most column indicates the total lower and higher reading of INR (9) measured against the total samples (87) so as to derive a percentage (9/87=10%).

From a review of Tables 4A and 4B it is realized that a discordance of 6–25% is obtained by the practice of this invention which is much better than the 17–29% described in the V. L. NG et al technical article.

Calibration of ATF

In the practice of this invention it is preferred that when a new lot of thromboplastin is to be used, it is desired to reestablish the mean normal prothrombin time MNPT so as to compute an INR value for each patient. For such a reestablishment, it is preferred that the circuit arrangement of FIG. 1 be calibrated. To accomplish such calibration, the specimens that are used to derive the MNPT are pooled to establish the low ATF value of the new lot in a manner as hereinbefore described. A pool of patients who have been on oral anticoagulants for at least 6 weeks, and ideally with an INR value of 3.0 or greater, is preferably used to establish the high ATF value. A run of at least 20 samples each of the high and low ATF pools establishes the instrument's precision as well as the MEAN(X), MEAN(Y) and SLOPE(X,Y) in a manner as hereinbefore described. These high and low ATF values are used to produce the modified ATF (MATF) value and are specific for each thromboplastin. These low and high ATF values are used as references to compare against when the new lot of thromboplastins are analyzed by the practice of the present invention to obtain both the ATF and CATF hereinbefore discussed.

In the practice of the present invention, the above calibration procedure was performed using Thromboplastin C+ of Dade Corporation and satisfactory results were obtained, although the slope and intercept quantities were not exactly 1 and 0 respectively.

It should now be appreciated that the practice of the present invention provides for methods and apparatuses to derive an anticoagulant therapy factor (ATF), a corrected anticoagulant therapy factor (CATF), and a modified anticoagulant therapy factor (MATF), all of which correlate well with the International Normalized Ratio (INR), yet do not suffer from the inaccuracy contributed to by the various thromboplastins derived from either rabbit or bovine brain.

While the invention has been described with reference to specific embodiments, the description is illustrative and is not to be construed as limiting the scope of the invention. Various modifications and changes may occur to those skilled in the art without departing from the spirit and scope of the invention as defined by the appended claims.

What we claim is:

1. A method of determining an anticoagulant therapy factor (ATF) comprising the steps of:
    (a) developing a series of analog electrical voltage signals having voltage amplitudes proportional to an optical density of a liquid sample containing fibrinogen;
    (b) converting the developed analog voltage signals into a series of digital voltage signals each having a value;
    (c) injecting a coagulant into the liquid sample, thereby producing an abrupt change in the optical density of the liquid sample, said abrupt change producing an abrupt change in the amplitude of the analog electrical voltage signals which, in turn, produces an abrupt change in the corresponding value of the corresponding digital voltage signal, the values of said digital voltage signals being directly indicative of fibrinogen concentration in the liquid sample;
    (d) recording an instant time $t_0$ of said abrupt change in said value of said digital voltage signal;
    (e) monitoring said digital voltage signal values for a first predetermined fibrinogen concentration quantity $c_1$;
    (f) recording an instant time $t_1$ and the value of the digital voltage signal of said first predetermined fibrinogen concentration quantity $c_1$:
    (g) recording an elapsed time between $t_0$ and $t_1$ which defines a prothrombin time (PT);
    (h) monitoring for a differential change in the digital voltage signal values that include a second predetermined fibrinogen concentration quantity $c_2$ which is at least equal to said first predetermined fibrinogen concentration quantity $c_1$, and a third predetermined fibrinogen concentration quantity $c_3$, said first $c_1$ and second $c_2$ predetermined fibrinogen concentration quantities occurring within a first predetermined time period $T_a$, said second $c_2$ and third $c_3$ predetermined fibrinogen concentration quantities occurring within a second predetermined time period $T_b$; and
    (i) recording an instant time and a digital voltage signal value for each of said second $c_2$, and third $c_3$ predetermined fibrinogen concentration quantities corresponding to times $t_2$ and $t_3$, said first predetermined time period $T_a$ being defined by the time difference between the instant times of said first $c_1$ and second $c_2$ predetermined fibrinogen concentration quantities, said second predetermined time period $T_b$ being defined by the time difference between the instant times $t_2$ and $t_3$ of said second $c_2$, and third $c_3$ predetermined fibrinogen concentration quantities, said third fibrinogen concentration quantity $c_3$ and said time $t_3$ defining a maximum acceleration point (MAP) and a time to maximum acceleration (TMA) being measured as the elapsed time from $t_1$ to $t_3$ which serves as a multiplier (TMA)/100, respectively and each of the third quantity $c_3$ and said time $t_3$ having a predetermined range starting prior to and ending after said maximum acceleration point (MAP) with the difference covered by an overall range defining a fibrinogen transformation rate (FTR);
    wherein the anticoagulant therapy factor (ATF) is expressed by the following relationship:

$$ATF=(PT/FTR)*(TMA/100).$$

2. The method according to claim 1, wherein said liquid sample is blood plasma.

3. The method according to claim 1, wherein the coagulant which is injected into the sample is thromboplastin with calcium ion.

4. The method according to claim 1, wherein the analog electrical voltage signal is developed by transmitting a light beam through a plasma sample and sensing the variations in light passing therethrough to develop corresponding variations in the electrical signal produced.

5. The method according to claim 1, wherein the overall range has a value from about 0.2 seconds to about 10.0 seconds so that the predetermined range both prior to and after the maximum acceleration point (MAP) has a value from about 0.1 seconds to about 5.0 seconds.

6. An apparatus for determining an anticoagulant therapy factor (ATF) comprising;

(a) means including a light source, a test tube, a photocell, a battery, and a variable resistor all for developing an analog electric voltage signal having an amplitude proportional to an optical density of a liquid sample containing fibrinogen;

(b) means including an A/D converter and a computer both cooperating for converting and recording the developed analog signal into a series of digital voltage signals each havina a value;

(c) means for injecting a coagulant into a liquid sample, thereby producing an abrupt change in the optical density of the liquid sample, said abrupt change producing a change in the amplitude of the analog electrical voltage signals, which, in turn, produces an abrupt change in the corresponding value of the corresponding digital voltage signal, the value of said digital voltage signals being directly indicative of fibrinogen concentration in the liquid sample;

(d) means for recording an instant time $t_0$ of said abrupt change in said value of said digital voltage signal;

(e) means for monitoring said digital voltage signal values for a first predetermined fibrinogen concentration quantity $c_1$;

(f) means for recording an instant time $t_1$ and the value of the digital voltage signal of said first predetermined fibrinogen concentration quantity $c_1$;

(g) means for recording an elapsed time between $t_0$ and $t_1$ which defines a prothrombin time (PT);

(h) means, including said computer, for monitoring said digital voltage signal values to determine a differential change in the digital voltage signal values that include a second predetermined fibrinogen concentration quantity $c_2$ which is at least equal to said first predetermined fibrinogen concentration quantity $c_1$ and a third predetermined fibrinogen concentration quantity $c_3$, and a fourth predetermined fibrinogen concentration quantity $c_4$, said first $c_1$ and second $c_2$ predetermined fibrinogen concentration quantities occurring within a first predetermined time period $T_a$, said second, $c_2$, and third, $c_3$, predetermined fibrinogen concentration quantities occurring within a second predetermined time period $T_b$, and said first, $c_1$, and said fourth, $c_4$, predetermined fibrinogen concentration quantities occurring within a third predetermined time period $T_c$;

(i) means for recording an instant time and digital voltage signal value for each of said second $c_2$, third $c_3$ and fourth $c_4$ predetermined fibrinogen concentration quantities corresponding to times $t_2$, $t_3$ and $t_4$ respectively, said first predetermined time period $T_a$ being defined by the time difference between the instant times of said first $c_1$ and second $c_2$ predetermined fibrinogen concentration quantities, said second predetermined time period $T_b$ being defined by the time difference between the instant time of said second $c_2$ and third $c_3$ predetermined fibrinogen concentration quantities, said third fibrinogen concentration quantity $c_3$ and said time $t_3$ defining a maximum acceleration point (MAP) and a time to maximum acceleration (TMA) being measured as the elapsed time from $t_1$ to $t_3$ which serves as a multiplier (TMA)/100, respectively, and each of the third quantity $c_3$ and said time $t_3$ having a predetermined range occurring both prior to and after said maximum acceleration point (MAP) with the difference covered by an overall range defining a fibrinogen transformation rate (FTR), and said predetermined time period $T_c$ being defined by the time difference between the instant times of said first $c_1$ and fourth $c_4$ predetermined fibrinogen concentration quantities; and (j) means, including said computer, for dividing the prothrombin time (PT) by the fibrinogen transformation rate (FTR) and the quotient being multiplied by the time to maximum acceleration (TMA) 100 with the product thereof being the anticoagulant therapy factor (ATF) expressed by the following relationship:

$$ATF=(PT/FTR)*(TMA/100).$$

7. The apparatus according to claim 6, wherein said liquid sample is blood plasma.

8. The apparatus according to claim 6, wherein said coagulant which is injected into the sample is thromboplastin with calcium ion.

9. The apparatus according to claim 6, wherein the analog electrical voltage signal is developed by transmitting a light beam through a plasma sample and sensing the variations in light passing therethrough to develop corresponding variations in the electrical signal produced.

10. The apparatus according to claim 6, wherein the overall range has a value from about 0.2 seconds to about 10.0 seconds so that the predetermined range both prior to and after the maximum acceleration point (MAP) has a value from about 0.1 seconds to about 5.0 seconds.

11. A method of determining a corrected anticoagulant therapy factor (CATF) comprising the steps of:

(a) developing a series of analog electrical voltage signals having voltage amplitudes proportional to respective optical densities of a plurality of liquid samples containing fibrinogen;

(b) converting the developed analog voltage signals into a series of digital voltage signals each having a value;

(c) injecting a coagulant into each of said plurality of liquid samples, thereby producing a respective abrupt change in the optical density of each of the liquid samples, said abrupt respective changes producing abrupt changes in the amplitude of the respective analog electrical voltage signals which, in turn produce abrupt changes in the values of the corresponding digital voltage signals, the values of said digital voltage signals being directly indicative of fibrinogen concentration in said plurality of liquid samples;

(d) recording an instant time to of each of said respective abrupt changes in said values of said digital voltage signals;

(e) monitoring each of said respective digital voltage signal values for a respective first predetermined fibrinogen concentration quantity $c_1$;

(f) recording an instant time $t_1$ and the value of the digital voltage signal of each of said respective first predetermined fibrinogen concentration quantity $c_1$;

(g) recording an elapsed time between $t_0$ and $t_1$ which defines a prothrombin time (PT) for each of said respective digital voltage signals;

(h) monitoring for a differential change in each of said respective digital voltage signal values that include a second predetermined fibrinogen concentration quantity $c_2$ which is at least equal to said respective first predetermined fibrinogen concentration quantity $c_1$, and a third predetermined fibrinogen concentration quantity $c_3$ for each of said respective digital voltage signal values, said first $c_1$ and second $c_2$ for each of said respective predetermined fibrinogen concentration quantities occurring within a first predetermined time period $T_a$, said second $c_2$ and third $c_3$ predetermined respective fibrinogen concentration quantities occurring within a second predetermined time period $T_b$; and (i) recording an instant time and digital voltage signal value for each of said respective second $c_2$ and third $c_3$ predetermined fibrinogen concentration quantities corresponding to times $t_2$ and $t_3$ for each of said respective digital voltage signal values, said first predetermined time period $T_a$ for each of said respective quantities being defined by the time difference between the instant times of said first $c_1$ and second $c_2$ of each of said respective predetermined fibrinogen concentration quantities, said second predetermined time period $T_b$ of each of said respective quantities being defined by the time difference between the instant times $t_2$ and $t_3$ of said second $c_2$ and third $c_3$ of each of said respective predetermined fibrinogen concentration quantities, said third fibrinogen concentration quantity $c_3$ and said time $t_3$ for each of said respective quantities defining a maximum acceleration point (MAP) for each of said respective quantities and a time to maximum acceleration (TMA) for each of said respective quantities being measured as the elapsed time from $t_1$ to $t_3$ for each of said respective quantities which serves as a multiplier (TMA)/100, respectively, and each of the third quantity $c_3$ and said time $t_3$ for each of said respective quantities having a predetermined range starting prior to and ending after said maximum acceleration point (MAP) with the difference covered by an overall range for each of said respective quantities defining a fibrinogen transformation rate (FTR) for each of said respective quantities;

wherein the corrected anticoagulant therapy factor (CATs) for each of said plurality of liquid samples is expressed by the following relationship:

$$CATF = \left(\frac{(PT)*(PR)}{FTR}\right)*\left(\frac{TMA}{100}\right)$$

where $$PR = \frac{PT}{MNPT}$$

and PR is the prothrombin ratio of the respective liquid sample and MNPT is the mean of the PT of the plurality of liquid samples from at least twenty (20) normal people.

12. The method according to claim 11, wherein said plurality of liquid samples is at least 20.

13. The method according to claim 11, wherein said liquid samples are blood plasma.

14. The method according to claim 11, wherein the coagulant which is injected into each of the plurality of samples is thromboplastin with calcium ion.

15. The method according to claim 11, wherein the analog electrical voltage signals are developed by transmitting a light beam through respective plasma samples and sensing the variations in light passing therethrough to develop corresponding variations in the electrical signal produced.

16. The method according to claim 11, wherein the overall range has a value from about 0.2 seconds to about 10.0 seconds so that the predetermined range both prior to and after the maximum acceleration point (MAP) has a value from about 0.1 seconds to about 5.0 seconds.

17. An apparatus for determining a corrected anticoagulant therapy factor (CATF) comprising:

(a) means including a light source, a test tube, a photocell, a battery, and a variable resistor all for developing analog electric voltage signals having an amplitude respectively proportional to optical densities of a plurality of liquid samples each containing fibrinogen;

(b) means including an A/D converter and a computer both cooperating for converting and recording the developed analog signals into a series of digital voltage signals each having a value;

(c) means for injecting a coagulant into each of said plurality of liquid samples, thereby producing a respective abrupt change in the optical density of each of the liquid samples, said abrupt respective changes producing changes in the amplitude of the respective analog electrical voltage signals, which, in turn, produce abrupt changes in the corresponding value of each of said respective corresponding digital voltage signals, the values of said digital voltage signals being directly indicative of fibrinogen concentration in each of said plurality of liquid samples;

(d) means for recording an instant time $t_0$ of each of said respective abrupt changes in said values of said digital voltage signals;

(e) means for monitoring each of said respective digital voltage signal values for a respective first predetermined fibrinogen concentration quantity $c_1$;

(f) means for recording an instant time $t_1$ and the value of the digital voltage signal of each of said first predetermined fibrinogen concentration quantity $c_1$;

(g) means for recording an elapsed time between $t_0$ and $t_1$ which defines a prothrombin time (PT) for each of said respective digital voltage signals;

(h) means, including said computer, for monitoring said digital voltage signal values to determine a differential change in each of said respective digital voltage signal values that include a second predetermined fibrinogen concentration quantity $c_2$ which is at least equal to said respective first predetermined fibrinogen concentration quantity $c_1$, a third predetermined fibrinogen concentration quantity $c_3$ for each of said respective digital voltage signal values, and a fourth predetermined fibrinogen concentration quantity $c_4$ for each of said respective digital voltage signal values, said first $c_1$ and second $c_2$ predetermined fibrinogen concentration quantities of each of said respective quantities occurring within a first predetermined time period $T_a$, said second $c_2$ and third $c_3$ predetermined fibrinogen concentration quantities of each of said respective quantities occurring within a second predetermined time period $T_b$, and said first $c_1$, and said fourth $c_4$, predetermined fibrinogen concentration quantities of each of said respective quantities occurring within a third predetermined time period $T_c$;

(i) means for recording an instant time and digital voltage signal value for each of said respective second $c_2$, third $c_3$ and fourth $c_4$ predetermined fibrinogen concentration quantities of each of said respective quantities corresponding to times $t_2$, $t_3$ and $t_4$, respectively, said first predetermined time period $T_a$ of each of said respective quantities being defined by the time difference between the instant times of said first $c_1$ and second $c_2$ of each of said respective predetermined fibrinogen concentration quantities, said second predetermined time period $T_b$ of each of said respective quantities being defined by the time difference between the instant time of said second $c_2$ and third $c_3$ of each of said respective predetermined fibrinogen concentration quantities, said third fibrinogen concentration quantity $c_3$ and said time $t_3$ for each of said respective quantities defining a maximum acceleration point (MAP) for each of said respective quantities and a time to maximum acceleration (TMA) for each of said respective quantities being measured as the elapsed time from $t_1$ to $t_3$ for each of said respective quantities which serves as a multiplier (TMA)/100, and each of the third quantity $c_3$ and said time $t_3$ for each of said respective quantities having a predetermined range occurring both prior to and after said maximum acceleration point (MAP) with the difference covered by an overall range defining a fibrinogen transformation rate (FTR), and said predetermined time period $T_c$ for each of said respective quantities being defined by the time difference between the instant times of said first $c_1$ and fourth $c_4$ of each of said predetermined fibrinogen concentration quantities; and (j) means including said computer for:
determining the quantity $$PR = \frac{PT}{MNPT}$$

for each of said plurality of said liquid samples, where PR is the prothrombin ratio of each of said plurality of said liquid samples and MNPT is the mean of the PT from the plurality of liquid samples; and determining the quantity $$\left(\frac{PT*PR}{FTR}\right)$$

for each of said plurality of said liquid samples;
wherein the corrected anticoagulant therapy factor (CATF) for each of said plurality of liquid samples is expressed by the following relationship:

$$CATF = \left(\frac{(PT)*(PR)}{FTR}\right) \times \left(\frac{TMA}{100}\right)$$

18. The apparatus according to claim 17, wherein said plurality of liquid samples is at least twenty (20).

19. The apparatus according to claim 17, wherein said liquid samples are blood plasma.

20. The apparatus according to claim 17, wherein said coagulant which is injected into each of the plurality of samples is thromboplastin with calcium ion.

21. The apparatus according to claim 17, wherein the analog electrical voltage signals are developed by transmitting a light beam through a plasma sample for each of said plurality of samples and sensing the variations in light passing therethrough to develop corresponding variations in the electrical signal produced.

22. The apparatus according to claim 17, wherein the overall range has a value from about 0.2 seconds to about 10.0 seconds so that the predetermined range both prior to and after the maximum acceleration point (MAP) has a value from about 0.1 seconds to about 5.0 seconds.

23. A method for determining a corrected anticoagulant therapy factor (CATF) for thromboplastin specimens comprising the steps of:

(a) determining the anticoagulant therapy factor (AFT) of at least twenty (20) specimens of said thromboplastin specimens by performing the following steps and selecting the AFT having the lowest value:

developing a series of analog electrical voltage signals having voltage amplitudes proportional to an optical density of a liquid sample containing fibrinogen;

converting the developed analog voltage signals into a series of digital voltage signals each having a value;

injecting a coagulant into the liquid sample, thereby producing an abrupt change in the optical density of the liquid sample, said abrupt change producing an abrupt change in the amplitude of the analog electrical voltage signals which, in turn, produces an abrupt change in the corresponding value of the corresponding digital voltage signal, the values of said digital voltage signals being directly indicative of fibrinogen concentration in the liquid sample;

recording an instant time $t_0$ of said abrupt change in said value of said digital voltage signal;

monitoring said digital voltage signal values for a first predetermined fibrinogen concentration quantity $c_1$;

recording an instant time $t_1$ and the value of the digital voltage signal of said first predetermined fibrinogen concentration quantity $c_1$;

recording an elapsed time between $t_0$ and $t_1$ which defines a prothrombin time (PT);

monitoring for a differential change in the digital voltage signal values that include a second predetermined fibrinogen concentration quantity $c_2$ which is at least equal to said first predetermined fibrinogen concentration quantity $c_1$, and a third predetermined fibrinogen concentration quantity $c_3$, said first $c_1$ and second $c_2$ predetermined fibrinogen concentration quantities occurring within a first predetermined time period $T_a$, said second $c_2$ and third $c_3$ predetermined fibrinogen concentration quantities occurring within a second predetermined time period $T_b$; and recording an instant time and a digital voltage signal value for each of said second $c_2$, and third $c_3$ predetermined fibrinogen concentration quantities corresponding to times $t_2$ and $t_3$, said first predetermined time period $T_a$ being defined by the time difference between the instant times of said first $c_1$ and second $c_2$ predetermined fibrinogen concentration quantities, said second predetermined time period $T_b$ being defined by the time difference between the instant times $t_2$ and $t_3$ of said second $c_2$, and third $c_3$ predetermined fibrinogen concentration quantities, said third fibrinogen concentration quantity $c_3$ and said time $t_3$ defining a maximum acceleration point (MAP) and a time to maximum acceleration (TMA) being measured as the elapsed time from $t_1$ to $t_3$ which serves as a multiplier (TMA)/100, respectively, and each of the third quantity $c_3$ and said time $t_3$ having a predetermined range starting prior to and ending after said maximum acceleration point (MAP) with the difference covered by an overall range defining a fibrinogen transformation rate (FTR);

wherein the anticoagulant therapy factor (ATF) is expressed by the following relationship:

$ATF = (PT/FTR)*(TMA/100);$ (b) determining the anticoagulant therapy factor (ATF) of at least twenty (20) specimens from a pool of patients that has been receiving oral anticoagulants for at least six (6) weeks by performing the following steps and selecting the AFT having the highest value:
developing a series of analog electrical voltage signals having voltage amplitudes proportional to an optical density of a liquid sample containing fibrinogen;
converting the developed analog voltage signals into a series of digital voltage signals each having a value;
injecting a coagulant into the liquid sample, thereby producing an abrupt change in the optical density of the liquid sample, said abrupt change producing an abrupt change in the amplitude of the analog electrical voltage signals which, in turn, produces an abrupt change in the corresponding value of the corresponding digital voltage signal, the values of said digital voltage signals being directly indicative of fibrinogen concentration in the liquid sample;
recording an instant time $t_0$ of said abrupt change in said value of said digital voltage signal;
monitoring said digital voltage signal values for a first predetermined fibrinogen concentration quantity $c_1$;
recording an instant time $t_1$ and the value of the digital voltage signal of said first predetermined fibrinogen concentration quantity $c_1$;
recording an elapsed time between $t_0$ and $t_1$ which defines a prothrombin time (PT);
monitoring for a differential change in the digital voltage signal values that include a second predetermined fibrinogen concentration quantity $c_2$ which is at least equal to said first predetermined fibrinogen concentration quantity $c_1$, and a third predetermined fibrinogen concentration quantity $c_3$, said first $c_1$ and second $c_2$ predetermined fibrinogen concentration quantities occurring within a first predetermined time period $T_a$, said second $c_2$ and third $c_3$ predetermined fibrinogen concentration quantities occurring within a second predetermined time period $T_b$; and
recording an instant time and a digital voltage signal value for each of said second $c_2$, and third $c_3$ predetermined fibrinogen concentration quantities corresponding to times $t_2$ and $t_3$, said first predetermined time period $T_a$ being defined by the time difference between the instant times of said first $c_1$ and second $c_2$ predetermined fibrinogen concentration quantities, said second predetermined time period $T_b$ being defined by the time difference between the instant times $t_2$ and $t_3$ of said second $c_2$, and third $c_3$ predetermined fibrinogen concentration quantities, said third fibrinogen concentration quantity $c_3$ and said time $t_3$ defining a maximum acceleration point (MAP) and a time to maximum acceleration (TMA) being measured as the elapsed time from $t_1$ to $t_3$ which serves as a multiplier (TMA)/100, respectively, and each of the third quantity $c_3$ and said time $t_3$ having a predetermined range starting prior to and ending after said maximum acceleration point (MAP) with the difference covered by an overall range defining a fibrinogen transformation rate (FTR);

wherein the anticoagulant therapy factor (ATF) is expressed by the following relationship:

$ATF = (PT/FTR)*(TMA/100);$ (c) determining the corrected anticoagulant therapy factor (CATF) of each said thromboplastin specimens by performing the following steps:
developing a series of analog electrical voltage signals having voltage amplitudes proportional to respective optical densities of a plurality of liquid samples containing fibrinogen;
converting the developed analog voltage signals into a series of digital voltage signals each having a value;
injecting a coagulant into each of said plurality of liquid samples, thereby producing a respective abrupt change in the optical density of each of the liquid samples, said abrupt respective changes producing abrupt changes in the amplitude of the respective analog electrical voltage signals which, in turn produce abrupt changes in the values of the corresponding digital voltage signals, the values of said digital voltage signals being directly indicative of fibrinogen concentration in said plurality of liquid samples;
recording an instant time $t_0$ of each of said respective abrupt changes in said values of said digital voltage signals;
monitoring each of said respective digital voltage signal values for a respective first predetermined fibrinogen concentration quantity $c_1$;
recording an instant time $t_1$ and the value of the digital voltage signal of each of said respective first predetermined fibrinogen concentration quantity $c_1$;
recording an elapsed time between $t_0$ and $t_1$ which defines a prothrombin time (PT) for each of said respective digital voltage signals;
monitoring for a differential change in each of said respective digital voltage signal values that include a second predetermined fibrinogen concentration quantity $c_2$ which is at least equal to said respective first predetermined fibrinogen concentration quantity $c_1$, and a third predetermined fibrinogen concentration quantity $c_3$ for each of said respective digital voltage signal values, said first $c_1$ and second $c_2$ for each of said respective predetermined fibrinogen concentration quantities occurring within a first predetermined time period $T_a$, said second $c_2$ and third $c_3$ predetermined respective fibrinogen concentration quantities occurring within a second predetermined time period $T_b$; and
recording an instant time and digital voltage signal value for each of said respective second $c_2$ and third $c_3$ predetermined fibrinogen concentration quantities corresponding to times $t_2$ and $t_3$ for each of said respective digital voltage signal values, said first predetermined time period $T_a$ for each of said respective quantities being defined by the time difference between the instant times of said first $c_1$ and second $c_2$ of each of said respective predetermined fibrinogen concentration quantities, said second predetermined time period $T_b$ of each of said respective quantities being defined by the time difference between the instant times $t_2$ and $t_3$ of said second $c_2$ and third $c_3$ of each of said respective predetermined fibrinogen concentration quantities, said third fibrinogen concentration quantity $c_3$ and said time $t_3$ for each of said respective quantities defining a maximum acceleration point (MAP) for each of said respective quantities and a time to maximum acceleration (TMA) for each of said respective quantities being measured as the elapsed time from $t_1$ to $t_3$ for each of said respective quantities which serves as a multiplier (TMA)/100, respectively, and each of the third quantity $c_3$ and said time $t_3$ for each of said respective quantities having a predetermined range starting prior to and ending after said maximum acceleration point (MAP) with the difference covered by an overall range for each of said respective quantities defining a fibrinogen transformation rate (FTR) for each of said respective quantities;

wherein the corrected anticoagulant therapy factor (CATF) for each of said plurality of liquid samples is expressed by the following relationship:

$$CATF = \left(\frac{(PT)*(PR)}{FTR}\right) * \left(\frac{TMA}{100}\right)$$

where PR=PT/MNPT and PR is the prothrombin ratio of the respective liquid sample and MNPT is the mean of the PT of the plurality of liquid samples from at least twenty (20) normal people; and (d) comparing the CATF of step (c) against the lowest value of ATF of step (a) and highest value of ATF of step (b) so as to ensure the compared CATF is not less than the lowest ATF value or greater than the highest ATF value.

24. A method of determining a modified anticoagulant therapy factor (MATF) comprising the steps of:

(a) determining the international normalized ratio (INR) of at least twenty (20) specimens of thromboplastin specimens;

(b) determining the international normalized ratio (INR) of at least twenty (20) specimens from a pool of patients that has been receiving oral anticoagulants for at least six (6) weeks;

(c) determining the corrected anticoagulant therapy factor (CATF) of each said thromboplastin specimens by performing the following steps;

developing a series of analog electrical voltage signals having voltage amplitudes proportional to respective optical densities of a plurality of liquid samples containing fibrinogen;

converting the developed analog voltage signals into a series of digital voltage signals each having a value;

injecting a coagulant into each of said plurality of liquid samples, thereby producing a respective abrupt change in the optical density of each of the liquid samples, said abrupt respective changes producing abrupt changes in the amplitude of the respective analog electrical voltage signals which, in turn produce abrupt changes in the values of the corresponding digital voltage signals, the values of said digital voltage signals being directly indicative of fibrinogen concentration in said plurality of liquid samples;

recording an instant time $t_0$ of each of said respective abrupt changes in said values of said digital voltage signals;

monitoring each of said respective digital voltage signal values for a respective first predetermined fibrinogen concentration quantity $c_1$;

recording an instant time $t_1$ and the value of the digital voltage signal of each of said respective first predetermined fibrinogen concentration quantity $c_1$;

recording an elapsed time between $t_0$ and $t_1$ which defines a prothrombin time (PT) for each of said respective digital voltage signals;

monitoring for a differential change in each of said respective digital voltage signal values that include a second predetermined fibrinogen concentration quantity $c_2$ which is at least equal to said respective first predetermined fibrinogen concentration quantity $c_1$, and a third predetermined fibrinogen concentration quantity $c_3$ for each of said respective digital voltage signal values, said first $c_1$ and second $c_2$ for each of said respective predetermined fibrinogen concentration quantities occurring within a first predetermined time period $T_a$, said second $c_2$ and third $c_3$ predetermined respective fibrinogen concentration quantities occurring within a second predetermined time period $T_b$; and recording an instant time and digital voltage signal value for each of said respective second $c_2$ and third $c_3$ predetermined fibrinogen concentration quantities corresponding to times $t_2$ and $t_3$ for each of said respective digital voltage signal values, said first predetermined time period $T_a$ for each of said respective quantities being defined by the time difference between the instant times of said first $c_1$ and second $c_2$ of each of said respective predetermined fibrinogen concentration quantities, said second predetermined time period $T_b$ of each of said respective quantities being defined by the time difference between the instant times $t_2$ and $t_3$ of said second $c_2$ and third $c_3$ of each of said respective predetermined fibrinogen concentration quantities, said third fibrinogen concentration quantity $c_3$ and said time $t_3$ for each of said respective quantities defining a maximum acceleration point (MAP) for each of said respective quantities and a time to maximum acceleration (TMA) for each of said respective quantities being measured as the elapsed time from $t_1$ to $t_3$ for each of said respective quantities which serves as a multiplier (TMA)/100, respectively, and each of the third quantity $c_3$ and said time $t_3$ for each of said respective quantities having a predetermined range starting prior to and ending after said maximum acceleration point (MAP) with the difference covered by an overall range for each of said respective quantities defining a fibrinogen transformation rate (FTR) for each of said respective quantities;

wherein the corrected anticoagulant therapy factor (CATF) for each of said plurality of liquid samples is expressed by the following relationship:

$$CATF = \left(\frac{(PT)*(PR)}{FTR}\right) * \left(\frac{TMA}{100}\right)$$

where $$PR = \frac{PT}{MNPT}$$

and PR is the prothrombin ratio of the respective liquid sample and MNPT is the mean of the PT of the plurality of liquid samples from at least twenty (20) normal people;

(d) selecting all of INR values as x quantities and the CATF values as y quantities;

(e) determining the mean as the x quantities and classifying said x quantities as MEAN (X);

(f) determining the mean of the y quantities and classifying said y quantities as MEAN (Y);

(g) determining the slope between the MEAN (X) and MEAN (Y) and classifying the slope as SLOPE (X,Y); and (h) deterinining the quantity MATE by the following expression:

$$MATF = ((CATF - MEAN\ (Y))/SLOPE\ (XY) + MEAN\ (X).$$

* * * * *